(12) United States Patent
Skattebol et al.

(10) Patent No.: US 10,472,314 B2
(45) Date of Patent: Nov. 12, 2019

(54) PROCESS FOR THE PREPARATION OF VITAMIN K2

(71) Applicant: KAPPA BIOSCIENCE AS, Oslo (NO)

(72) Inventors: Lars Skattebol, Jar (NO); Inger Reidun Aukrust, Oslo (NO); Marcel Sandberg, Oslo (NO)

(73) Assignee: KAPPA BIOSCIENCE AS, Oslo (NO)

( * ) Notice: Subject to any disclaimer, the term of this patent is extended or adjusted under 35 U.S.C. 154(b) by 0 days.

(21) Appl. No.: 15/627,627

(22) Filed: Jun. 20, 2017

(65) Prior Publication Data

US 2017/0283354 A1   Oct. 5, 2017

Related U.S. Application Data

(60) Division of application No. 14/681,717, filed on Apr. 8, 2015, now abandoned, which is a continuation of application No. 13/119,585, filed as application No. PCT/GB2009/002282 on Sep. 24, 2009, now Pat. No. 9,012,693.

(30) Foreign Application Priority Data

Sep. 24, 2008 (GB) .................................. 0817528.3

(51) Int. Cl.
| | |
|---|---|
| *C07C 46/02* | (2006.01) |
| *C07C 41/18* | (2006.01) |
| *C07C 41/22* | (2006.01) |
| *C07C 41/26* | (2006.01) |
| *C07C 41/30* | (2006.01) |
| *C07C 50/14* | (2006.01) |
| *C07C 315/04* | (2006.01) |
| *C07C 319/20* | (2006.01) |
| *C07C 17/16* | (2006.01) |
| *C07C 43/215* | (2006.01) |
| *C07C 46/04* | (2006.01) |
| *C07C 21/215* | (2006.01) |

(52) U.S. Cl.
CPC .............. *C07C 46/02* (2013.01); *C07C 17/16* (2013.01); *C07C 21/215* (2013.01); *C07C 41/18* (2013.01); *C07C 41/22* (2013.01); *C07C 41/26* (2013.01); *C07C 41/30* (2013.01); *C07C 43/215* (2013.01); *C07C 46/04* (2013.01); *C07C 50/14* (2013.01); *C07C 315/04* (2013.01); *C07C 319/20* (2013.01); *C07B 2200/13* (2013.01)

(58) Field of Classification Search
CPC .......... C07C 46/02; C07C 46/04; C07C 41/18
See application file for complete search history.

(56) References Cited

U.S. PATENT DOCUMENTS

| | | |
|---|---|---|
| 4,089,873 A | 5/1978 | Rapoport et al. |
| 4,159,993 A | 7/1979 | Rapoport et al. |
| 4,199,531 A | 4/1980 | Kato et al. |
| 4,234,746 A | 11/1980 | Rapoport et al. |
| 4,270,003 A | 5/1981 | Fujita et al. |
| 5,086,189 A | 2/1992 | Lecloux et al. |

(Continued)

FOREIGN PATENT DOCUMENTS

CN      101029003      9/2007

OTHER PUBLICATIONS

International Search Report for PCT/GB2009/002282, dated Feb. 5, 2010.

(Continued)

*Primary Examiner* — Pancham Bakshi
(74) *Attorney, Agent, or Firm* — Nixon & Vanderhye P.C.

(57) ABSTRACT

Using a combination of Kumada, Suzuki and Biellmann chemistry, various menaquinones can synthesized rapidly and with stereochemical integrity offering a new way of preparing these vitamin K2 components for the pharmaceutical market. In one embodiment a process for the preparation of a compound of formula (I)

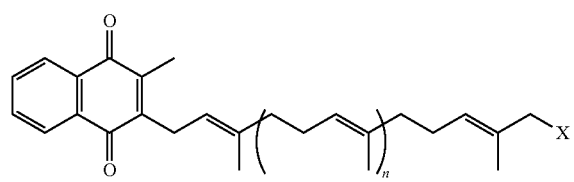

is defined including a step in which (i) a compound of formula (II) is reacted with a compound of formula (III)

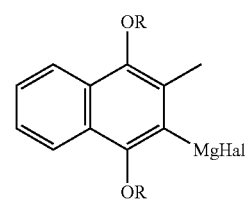

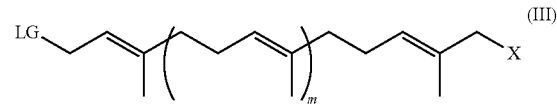

wherein R is an alkyl group;
LG is a leaving group;
m is an integer from 0 to 8;

(Continued)

n is an integer of from 0 to 9; and
X is hydrogen, halide, hydroxyl or protected hydroxyl;
in the presence of a copper, nickel or palladium catalyst.

1 Claim, No Drawings

(56) References Cited

U.S. PATENT DOCUMENTS

| | | | |
|---|---|---|---|
| 5,229,385 A * | 7/1993 | Terao | C07D 213/50 514/235.5 |
| 9,012,693 B2 | 4/2015 | Skattbol | |
| 2008/0220094 A1 | 9/2008 | Bobyock et al. | |

OTHER PUBLICATIONS

Written Opinion of the International Searching Authority for PCT/GB2009/002282, dated Feb. 5, 2010.
Tso, H-H et al., "A Convenient One-flask Synthesis of Vitamin K", Journal of Chemical Research, (Jan. 1, 1995), pp. 104-105.
Masaki, Y. et al., "Synthetic Studies on Isoprenoidquinones. II. Syntheses of Ubiquinone-10, Phylloquinone, and Menaquinone-4 by a Chain-Extending Method Utilizing Terminally Functionalized Isoprenoidhydroquinones", Chemical and Pharmaceutical Bulletin, vol. 32, No. 10, (Jan. 1, 1984), pp. 3959-3967.
Altman, L.J. et al., "A New, Highly Stereoselective Synthesis of all trans-Geranylgeraniol", Synthesis, (Feb. 1974), pp. 129-131.
Snyder, Clinton D. et al., "Synthesis of Menaquinones", Journal of the American Chemical Society, 96:26, (Dec. 25, 1974), pp. 8045-8054.
Suhara, Y. et al., "Method for the Determination of Vitamin K Homologues in Human Plasma Using High-Performance Liquid Chromatography—Tandem Mass Spectrometry", Anal. Chem., vol. 77, (2005), pp. 757-763.
Suhara, Y. et al., "Efficient synthesis and biological evaluation of ω-oxygenated analogues of vitamin $K_2$:Study of modification and structure-activity relationship of vitamin $K_2$ metabolites", Bioorganic & Medicinal Chemistry Letters, No. 17, (2007), pp. 1622-1625.
Min, J-H et al., "The Friedel-Crafts Allylation of a Prenyl Group Stabilized by a Sulfone Moiety: Expeditious Synthesis of Ubiquinones and Menaquinones", J. Org. Chem., vol. 68, (2003), pp. 7925-7927.
Rosales, V. et al., "Regioselective Palladium-Catalyzed alkylation of Allylic Halides with Benzylic Grignard Reagents. Two-Step Synthesis of Abietane Terpenes and Tetracyclic Polyprenoid Compounds", J. Org. Chem., vol. 67, (2002), pp. 1167-1170.
Naruta, Y., Regio- and Stereoselective Synthesis of Coenzymes $Q_n$ (n=2-10), Vitamin K, and Related Polyprenylquinones[1], J. Org. Chem., vol. 45, (1980), pp. 4097-4104.
Snyder, C.D. et al., "Synthesis of Chlorobiumquinone1", J. Org. Chem., vol. 36, No. 25, (1971), pp. 3951-3960.
Takuwa, A. et al., "Stereochemistry in the Reactions of (Z)- and (E)-Allyltributylstannyl Reagents with Quinones", American Chemical Society, (1987), pp. 1261-1265.
Kaneki; Nutrition, vol. 17, No. 4, 2001, pp. 315-321.

* cited by examiner

PROCESS FOR THE PREPARATION OF VITAMIN K2

CROSS REFERENCE

This application is a divisional of U.S. patent application Ser. No. 14/681,717, filed Apr. 8, 2015, pending, which is a continuation of Ser. No. 13/119,585, filed Apr. 19, 2011 (U.S. Pat. No. 9,012,693) which is the U.S. National Phase of International Application No. PCT/GB2009/002282 filed Sep. 24, 2009 which designated the U.S. and claims priority to United Kingdom Application 0817528.3, filed Sep. 24, 2008, the entire contents of each of which are hereby incorporated by reference.

This application relates to the synthesis of a compound that forms part of vitamin K2, as well as the synthesis of some novel intermediate compounds. Vitamin K denotes a group of lipophilic and hydrophobic vitamins that are needed for the post-translational modification of certain proteins, mostly required for blood coagulation. Chemically they are 2-methyl-1,4-naphthoquinone derivatives.

Vitamin K is not a single compound, rather it is a series of related analogues. Vitamin K1 is called phylloquinone and has the systematic name all-E-2-methyl-3-(3,7,11,15-tetramethylhexadec-2-enyl)naphthalene-1,4-dione. Vitamin K2 (menaquinone) is normally produced by bacteria in the intestines, and dietary deficiency is extremely rare unless the intestines are heavily damaged or are unable to absorb the molecule.

Vitamin K2 is a mixture of different molecules based on a naphthoquinone structure and varying lengths of isoprenoid chains. The compound MK-7 (i.e. 7 isoprenyl groups) is depicted below but other components of the vitamin have different numbers of isoprenoid links. Menaquinones have side chains composed of all-E polyprenyl residues; generally they are designated as MK-n, where n specifies the number of isoprenoid repeating units. The minimum value of n is 2.

MK-7

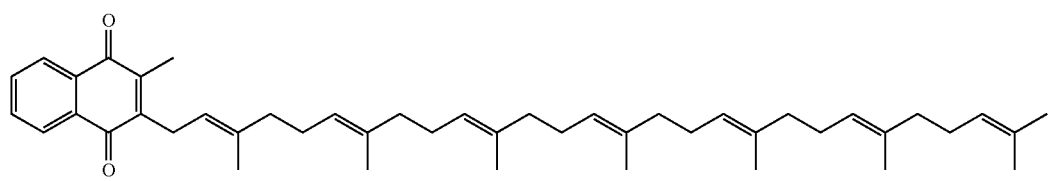

All members of the vitamin K group of vitamins share a methylated naphthoquinone ring structure, and vary in the aliphatic side chain attached at the 3-position.

It is generally accepted that the naphthoquinone is the main functional group of the vitamin, so that the mechanism of action is similar for all K-vitamins. Substantial differences may be expected, however, with respect to intestinal absorption, transport, tissue distribution, and bio-availability when variations in the side chain take place. These differences are caused by the different lipophilicity of the various side chains and by the different food matrices in which they occur.

A recent paper (Suhara et al., Biorganic Med. Chem Lett. 17 (2007) 1622-1625) suggests the use of certain vitamin K metabolites as biologically active compound which can lead to the development of new drugs based on side-chain modification of the alkyl group. Suhara targets compounds of structure similar to metabolites of vitamin K, i.e. compounds carrying acidic (or other strongly hydrophilic groups) at the terminus of the 3-position side chain. Some of the analogues have apoptosis-inducing properties.

It is known that γ-carboxylated osteocalcin is involved in the bone remodeling system, and there are strong indications that vitamin K has a beneficial effect on bone diseases such as osteoporosis. There is interest therefore in the investigation of various vitamin K2 type compounds for inhibitory effects on osteoporosis, as potential anti-cancer drugs and for beneficial cardio-vascular activity.

Whilst vitamin K2 occurs naturally in various vegetables and can be produced by bacteria in the intestines, it is still an interesting synthetic target as isolation of the vitamin from a natural source is complex and concentrations of the vitamin are low. Moreover, synthesis allows the preparation of particular menaquinones rather than the isolation of a mixture of different menaquinones.

Various individuals have synthesised the menaquinone compounds which form part of vitamin K2 or components thereof. The first synthesis of menaquinones, reported by Isler et al., Helv. Chim Acta 1958, 41, 786-807, used a nonstereospecific approach. Tso and Chen, J Chem Res 1995, 104-105 describes a one pot synthesis of vitamin K although he concentrates on the formation of the naphthoquinone ring as opposed to the side chain of the molecule. His chemistry involves the reaction of 3-substituted isobenzofuranones with vinylic sulphones to form the naphthoquinone ring structure.

Suhara et al, Bioorg Med Chem Lett 17, (2007) 1622-1625, describe various syntheses of menaquinone analogues in which the terminal methyl group is converted to a hydroxyl, aldehyde or acid group.

Naruta, J Org Chem 1980, 45, 4097-4104, describes the synthesis of some vitamin K2 analogues using trialkylallylstannane chemistry to bond the preformed side-chain to the naphthoquinone group.

The present inventors have devised a synthetic strategy for the formation of MK-7 and other menaquinones. The method utilises Kumada or Suzuki chemistry to connect a side chain to the naphthoquinone ring. In further embodiments, the side chain can be further manipulated, e.g. using Biellmann chemistry to produce the desired compounds.

The process of the invention allows formation of menaquinones in high yield and crucially with stereochemical integrity. In particular, the inventors do not see any presence of Z-isomers during their reactions.

KUMADA

Thus, viewed from a first aspect the invention provides a process for the preparation of a compound of formula (I)

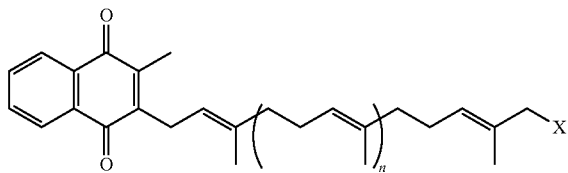

(I)

comprising a step in which (i) a compound of formula (II) is reacted with a compound of formula (III)

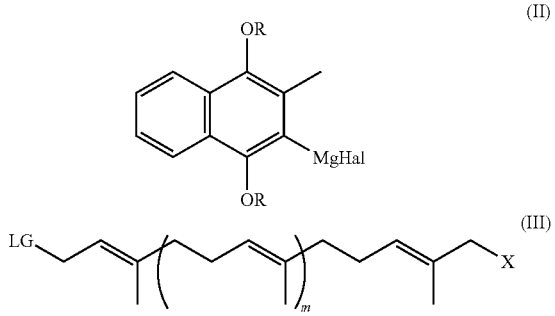

(II)

(III)

wherein R is an alkyl group;

LG is a leaving group;

m is an integer of from 0 to 8;

n is an integer of from 0 to 9; and

X is hydrogen, halide, hydroxyl, or protected hydroxyl;

in the presence of a copper, nickel or palladium catalyst.

SUZUKI

Viewed from a second aspect, the invention provides a process for the preparation of a compound of formula (I)

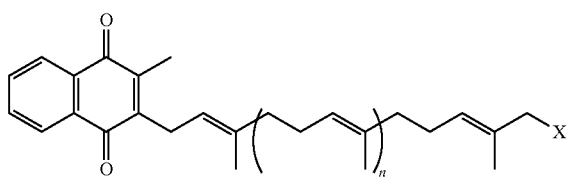

(I)

comprising a step in which (i) a compound of formula (IV)

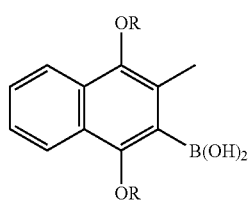

(IV)

where R is an alkyl group; is reacted with a compound of formula (III)

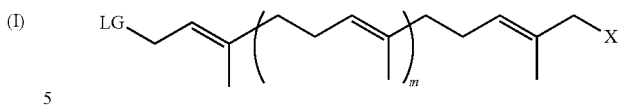

(I)

wherein LG is a leaving group, m is an integer of from 0 to 8, n is 0 to 9 and X is hydrogen, halide, hydroxyl, or optionally protected hydroxyl;

in the presence of a Pd (0) catalyst.

Biellmann

The successful use of either Kumada or Suzuki coupling for preparing the vitamin K2 compounds depends on the availability of a precursor for the all-E polyprenyl side chains. To reach this objective the inventors have employed Biellmann chemistry. This reaction involves the formation of phenythio or phenylsulfonyl substituted compounds and reaction of these sulphur compounds with an electrophile, such as a halide, in the presence of a base. Suitable bases include n-butyl lithium, tert butyl lithium, and non nucleophilic bases such as tertbutoxides. After coupling, the phenythio or phenylsulfonyl groups are removed reductively for example with lithium metal or a metal hydride. The inventors have found that this method is ideal for coupling together two isoprenoid chains to make a new isoprenoid chain of, for example, 7 or more units. This is a third aspect the invention.

The reaction of a compound of formula (II) or (IV) with a compound of formula (III) may however be only one step in the formation of a compound of formula (I). The reaction of compounds (II) and (III) or (II) and (IV) yields the compound (I')

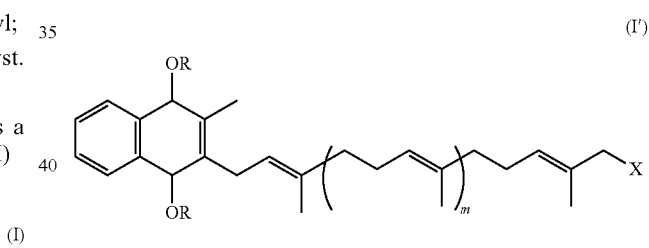

(I')

It will be appreciated that to complete the synthesis of a compound of formula (I) it is necessary to convert the diprotected naphthoquinone (I') back to naphthoquinone. This can be achieved by any convenient oxidation method although typically cerium ammonium nitrate (CAN) can be used.

The process of the invention may therefore incorporate further steps before or after the claimed reaction as described below in order to allow the formation of a compound of formula (I), especially MK-7.

Definitions

A polyprenyl side chain is one which derives from the polymerisation of isoprene: 2-methyl-1,3-butadiene.

Unless otherwise stated, an alkyl group can contain 1 to 6 carbon atoms, preferably 1 to 4 carbon atoms, especially methyl or ethyl. In all embodiments R is preferably methyl.

Halide (Hal) includes fluoro, chloro, bromo and iodo, preferably chloro or bromo. Halides employed as Grignard reagents are preferably bromo.

The term protecting group covers any known protecting group for the group in question. Hydroxyl protecting groups include acetyl (Ac), benzyl, β-methoxyethoxymethyl ether (MEM), methoxymethyl ether (MOM), p-methoxybenzyl ether (PMB), methylthiomethyl ether, pivaloyl (Piv), tetrahydropyran (THP), Silyl ether (most popular ones include trimethylsilyl (TMS), t-butyldimethylsilyl (TBDMS), and triisopropylsilyl (TIPS) ethers), and methyl ethers. In any embodiment of the invention, preferred protecting groups are benzyl or THP.

The term leaving group is well known in the art and denotes an atom or group of atoms that readily leaves a molecule due to the relative stability of the ion formed. Useful leaving groups include halides, tosylates, mesylates and triflates. In any embodiment of the invention, preferred leaving groups are halides.

In any embodiment of the invention "n" is 0 to 9, preferably 1 to 8, more preferably 4 to 7, e.g. 6, 7 or 8 isoprenoid units. In some embodiments n may range from 0 to 10 or 0 to 11.

In any embodiment of the invention "m" is 0 to 8, e.g. 0 to 7, preferably 0 to 5, more preferably 1 to 4, e.g. 2, 3 or 4 isoprenoid units. It will be appreciated that the sum of the various m values of the starting materials will add up to the value of n in the compound of formula (I) taking into account any units formed in the reactions in question. Thus if one isoprene unit is formed by the reactions then n-1 is the total of all m's. Where a reaction process involves multiple reactants in which the variable m is present, it will be appreciated that each m can be different.

In compounds of formula (I), X is preferably hydrogen.

DETAILED DESCRIPTION OF THE INVENTION

The present invention relates to the synthesis of compounds of formula (I), i.e. menaquinone derivatives having varying length of a polyprenyl side chain in their backbone. Whilst the length of the polyprenyl chain in the compound of formula (I) can vary, it is preferred if there are at least 6 isoprenoid units, more preferably at least 7 isoprenoid units in the compound of formula (I). It is preferred therefore if n is at least 3, preferably 4, 5 or 6.

The compound of formula (III) required to effect the reaction above can contain different numbers of isoprenoid units. The compound of formula (III) is typically not commercially available and itself needs to be synthesised from compounds with a smaller number of isoprenoid units. A particular challenge faced by the synthetic chemist is preparing menaquinone compounds having different numbers of isoprenoid units. In order to manufacture higher menaquinones, i.e. those of 7 isoprenoid units or more, it is normally necessary to have at least one reactant which comprises 4 or more isoprenoid units. Such compounds are still not readily available and therefore need to be synthesised themselves. It will be seen therefore that the synthesis of higher menaquinones is not simple. Starting from commercially available farnesol (A) methods have been devised for extending this molecule stereoselectively by one isoprenoid unit at a time (see Coates et al Org. Synth. 2007, 84, 43-57)

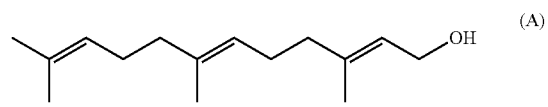 [SMILES: CC(C)=CCC/C(C)=C/CC/C(C)=C/CO]

(A)

However, where the number of units is high, it may not be practical to add just one unit at a time to compound (A). If 10 units are required, the overall yield of the process might be too low to be of commercial interest. The inventors have therefore sought more ways of forming the menaquinone side chain having multiple isoprenoid units.

The inventors have found that Biellmann chemistry, as described in the third aspect of the invention, provides an ideal way to make even longer vitamin K2 side chain molecules which can then be coupled to a naphthoquinone ring following the chemistry described in the first and second aspects described above. Alternatively this chemistry can be used to increase the size of a side chain already attached to the naphthoquinone ring.

The most common starting materials for the formation of the isoprenoid side chains are polyprenyl alcohols. It is possible to convert an alcohol into a better leaving group and effect addition of the phenylthio or phenylsulfonyl group via a nucleophilic attack of the thiophenyl ion or phenylsulfonyl-ion on the leaving group. For phenylthio group, the inventors have found another method based on the reaction of the alcohol directly with diphenyldisulfide in the presence of a trialkyl phosphine, e.g. PBu3.

The resulting phenythio or phenylsulfonyl substituted compounds are readily deprotonated with base forming the corresponding anions which can be reacted with a compound having a suitable leaving group yielding the basis of the isoprenoid carbon chain. Suitable bases include BuLi.

Scheme 1 examplifies this type of reaction with a bromide and a phenylthio substituted derivative.

Scheme 1

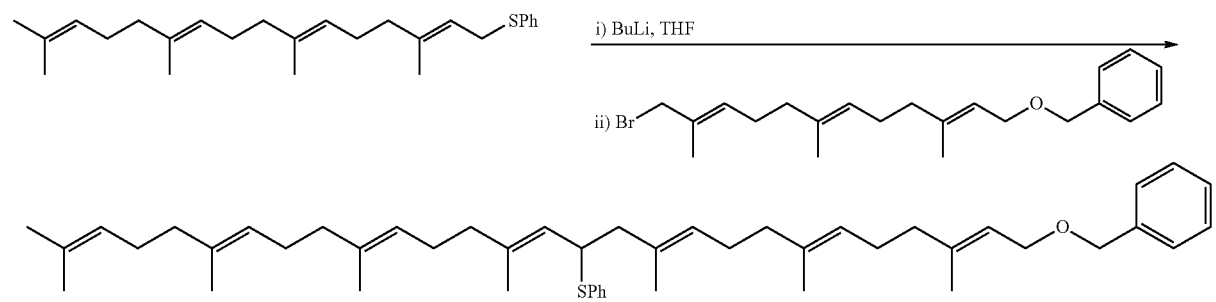

The bromide reactant in scheme 1 can be conveniently synthesised from farnesol (A). Protection of farnesol with a benzyl group allows the introduction of a terminal OH group using selenium dioxide in t-butylperoxide. This can then be converted to the bromide using known chemistry (scheme 2)

Scheme 2

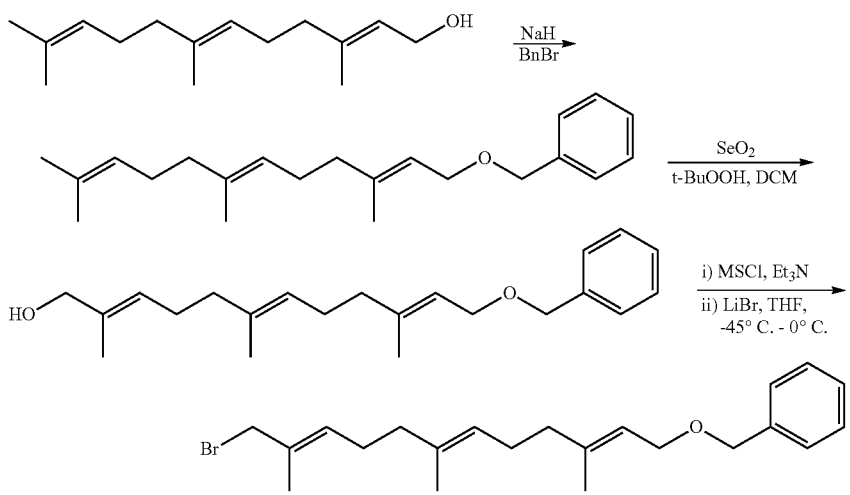

Once the coupling has been completed it is a preferred feature of the invention that reduction of the phenythio or phenylsulfonyl group also simultaneously removes any protection present, e.g. the benzyl protecting group leaving an alcohol. Reduction is conveniently effected using lithium metal in an amine solvent such as propylamine or ethylamine or using palladium catalysis with a borohydride, e.g. $PdCl_2(dppp)$ and lithium triethyl borohydride. Any other method for reduction of the phenythio or phenylsulfonyl group could also be employed.

Reduction of the product in scheme 1 yields compound XV

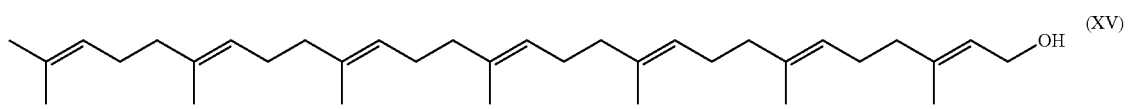 [SMILES: CC(C)=CCC/C(C)=C/CC/C(C)=C/CC/C(C)=C/CC/C(C)=C/CC/C(C)=C/CC/C(C)=C/CO]

which contains 7 isoprenoid units and is therefore a perfect precursor to the side chain of MK-7.

To complete the synthesis, the naphthoquinone group must be introduced. This compound can be prepared from commercially available 2-methylnaphtoquinone as starting material as outlined in scheme 3. This brominated intermediate is converted to its dimethoxy analogue using tin dichloride in ethanol and subsequent treatment with dimethylsulphate and base. This dimethoxy derivative can then form the corresponding Grignard reagent. This chemistry is well established (Snyder and Rapoport, J Am Chem. Soc 1974, 96, 8046-8054).

Scheme 3

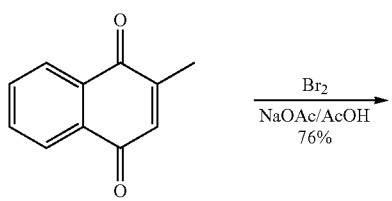

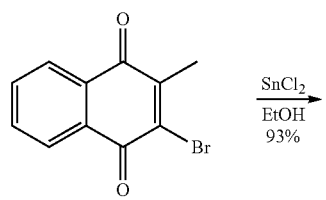

-continued

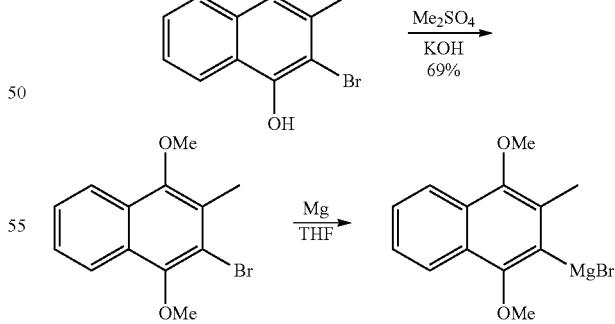

The alcohol XV is converted to a halide, but the subsequent coupling to the naphthoquinone derivative using a classical Grignard reaction is not very useful. It is highly preferred if the reaction of the naphthoquinone derivative with the isoprenyl side chain is effected by Kumada coupling chemistry, as described in the first aspect of the invention. The inventors have found that Kumada chemistry improves yields and again prevents any loss of stereochemistry during the formation of the menaquinone. The coupling proceeds smoothly and the menaquinone MK-7 was obtained after oxidation of the methoxy groups on the naphthoquinone ring by cerium ammonium nitrate (CAN) or other oxidation methods (scheme 4).

Scheme 4

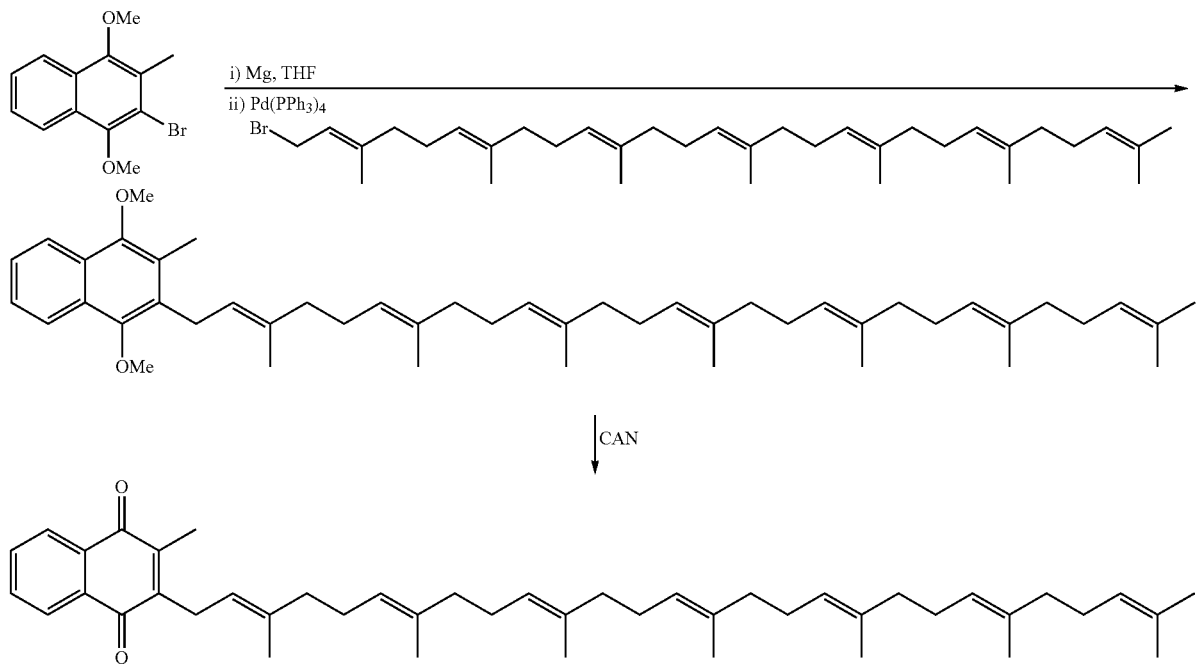

The catalyst used in the Kumada coupling can be a Cu (II), Ni (II) or (Pd(0) species. Suitable compounds include nickel chloride with two dppe ligands (NiCl$_2$(1,2-bis(diphenylphosphino)ethane)$_2$), nickel(II) acetylacetonate and tetrakis(triphenylphosphine)palladium(0). For a detailed discussion of Kumada chemistry see Yamamura, M., Moritani, I. and Murahashi, S-I. *Journal of Organometallic Chemistry*, 91 (2), 1975, C39-C42.

In another strategy leading to MK-7 the Kumada coupling is actually used twice as outlined in scheme 5. In the first Kumada coupling the Grignard reagent reacts with commercially available geranyl chloride providing the geranyl substituted derivative. Oxidation with SeO$_2$ affords the alcohol which is transformed into the bromide. The second Kumada coupling between this bromide and the Grignard reagent from pentaisoprenyl compound completed the synthesis of MK-7.

Scheme 5

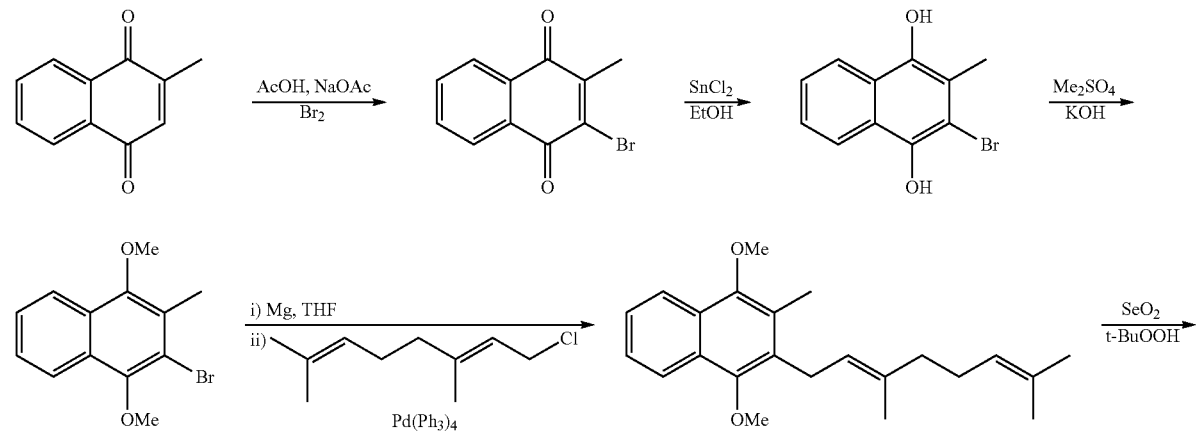

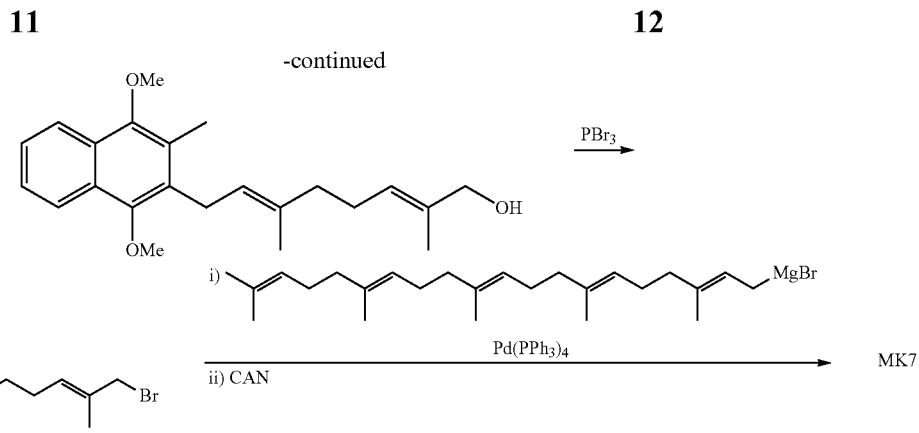

Scheme 5b is an alternative use of the Kumada coupling strategy using a prohydroxyl reactant during the Kumada coupling stage to readily afford a reactive X group for further reaction.

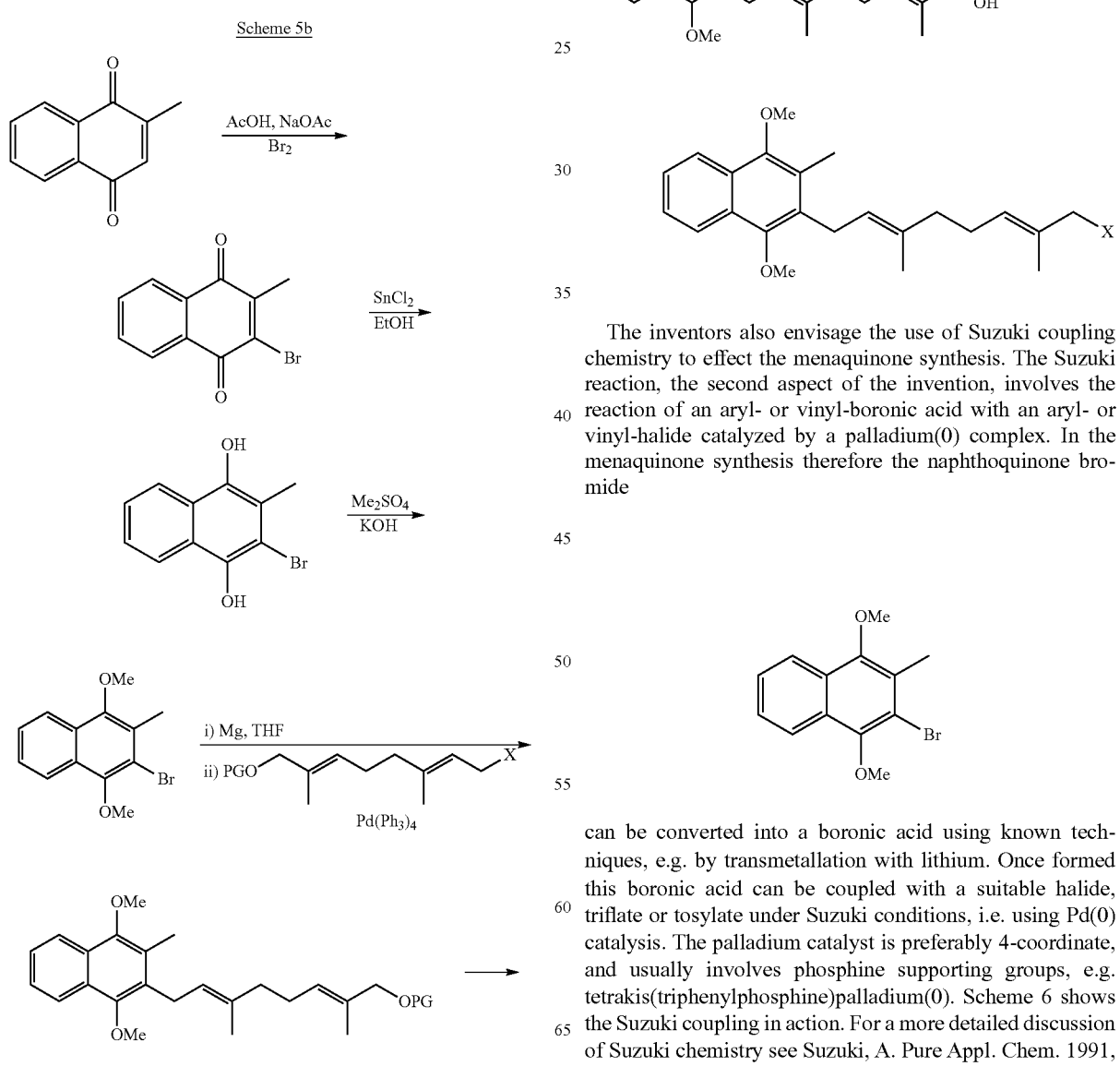

The inventors also envisage the use of Suzuki coupling chemistry to effect the menaquinone synthesis. The Suzuki reaction, the second aspect of the invention, involves the reaction of an aryl- or vinyl-boronic acid with an aryl- or vinyl-halide catalyzed by a palladium(0) complex. In the menaquinone synthesis therefore the naphthoquinone bromide can be converted into a boronic acid using known techniques, e.g. by transmetallation with lithium. Once formed this boronic acid can be coupled with a suitable halide, triflate or tosylate under Suzuki conditions, i.e. using Pd(0) catalysis. The palladium catalyst is preferably 4-coordinate, and usually involves phosphine supporting groups, e.g. tetrakis(triphenylphosphine)palladium(0). Scheme 6 shows the Suzuki coupling in action. For a more detailed discussion of Suzuki chemistry see Suzuki, A. Pure Appl. Chem. 1991, 63, 419-422.

Scheme 6

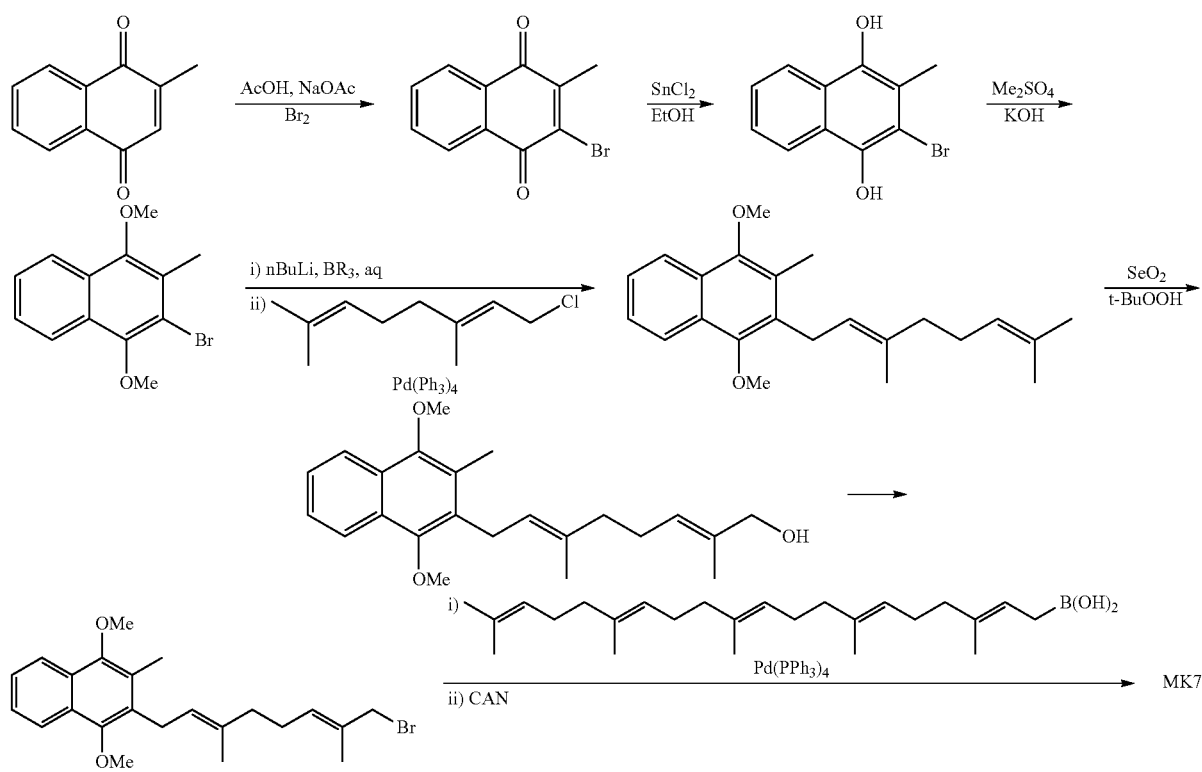

In scheme 6, Suzuki chemistry is used in the formation of the MK-7 compound. Moreover, both schemes 5 and 6 introduce an alternative method of forming the menaquinone side chain, i.e. by building it up actually on the naphthoquinone structure rather than preforming the entire side chain, as depicted in scheme 6.

It is a feature of the invention therefore that the reaction achieved in the first and second aspects of the invention, i.e. a Kumada or Suzuki coupling reaction can yield only a relatively short side chain which can then be built up to form a compound of formula (I). To complete the synthesis of a longer chain menaquinone further Kumada, Suzuki or any other chemistry can be used.

Viewed from another aspect therefore the invention further comprises a process for the preparation of a compound of formula (I)

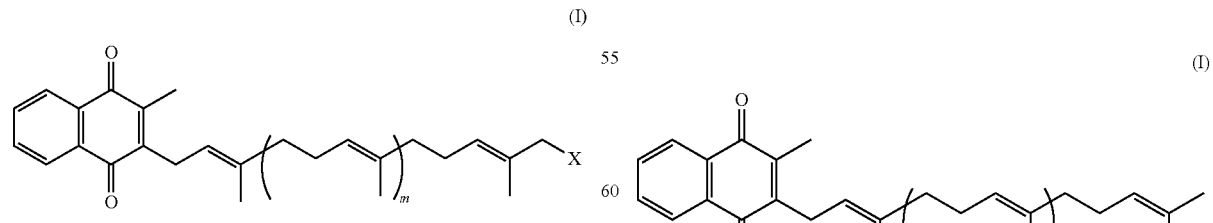

comprising (i) reacting a compound of formula (II) or (IV) with a compound of formula (III) as hereinbefore defined;
(iii) if necessary, converting X into a leaving group;
(iv) reacting with a compound

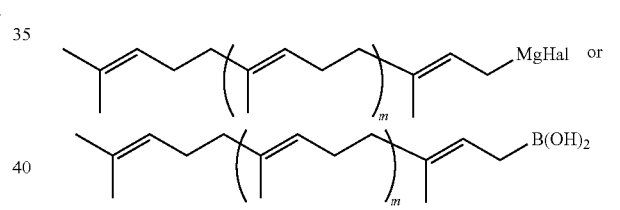

where m is independently as hereinbefore defined;
in the presence of a Ni, Cu or Pd catalyst; and
(v) converting the diprotected naphthoquinone into a naphthoquinone.

The catalyst used here is chosen depending on the reaction in question, e.g. Pd(0) for a Suzuki coupling, Cu(II), Ni (II) or Pd(0) for Kumada.

Viewed from another aspect therefore the invention further comprises a process for the preparation of a compound of formula (I)

comprising (i) reacting a compound of formula (II) or (IV) with a compound of formula (III) as hereinbefore defined;

(iii) if necessary, converting X into a leaving group;
(iv) reacting with a compound (V) or (VI)

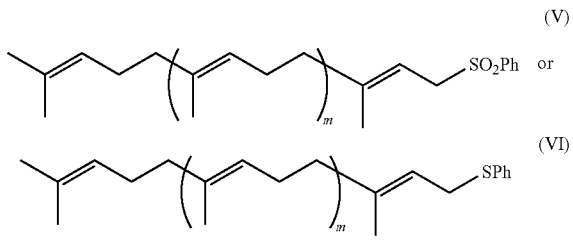

where m is independently as hereinbefore defined in the presence of a base;
(v) reductively removing the phenythio or phenylsulfonyl groups in the resulting compounds and
(vi) converting by oxidation the diprotected naphthoquinone into a naphthoquinone.

By varying the number of isoprene units in either molecule coupled using the Biellmann reaction, Suzuki coupling or Kumada coupling all manner of different menaquinone compounds can be produced. It will be appreciated therefore that the values of n in the reactants must be selected to match the number of repeating units desired in the compound of formula (I) bearing in mind, of course, that some isoprenoid units are formed during the reactions themselves. This will be readily achieved by the skilled man.

Ideally, MK-7 is produced especially where 2 units come from compound (III), 4 units from compound (V) or (VI) (the 7th being formed by the reaction). This is the most preferred process of the invention. The preferred process is therefore wherein any leaving group may be substituted for Br (e.g. other halogens, tosylate, mesylate etc). A benefit of preparing MK-7 using this "2+5" strategy is that the selenium dioxide reduction step used to form the napthoquinone reactant takes place more readily on a naphthoquinone carrying on 2 isoprenoid units than on a longer chain molecule. This "2+5" method also gives better stereochemistry and has been found to allow the formation of solid, in particular crystalline MK-7.

In a further embodiment, the inventors have realised that different side chains can be prepared using a double Biellmann coupling (or triple Bielmann etc). Initially, therefore two shorter chain molecules can be combined. By using appropriate protection strategies, the coupled species can then be deprotected to reveal an alcohol which can be converted to phenythio or phenylsulfonyl substituted compounds ready for a second Biellmann coupling. In this way, the isoprenoid units needed to form the complete side chain of a long menaquinone can be joined together from shorter starting blocks. Reduction of all phenythio or phenylsulfonyl substituted compounds present can take place as a final step to yield a side chain suitable for coupling to a naphthoquinone related molecule, e.g. using Kumada or Suzuki chemistry. This reaction is highly flexible and allows the formation of side chains for menaquinones such as MK-6, MK-7, MK-8, MK-9, MK-10 and MK-11.

One such reaction is depicted below in scheme 7

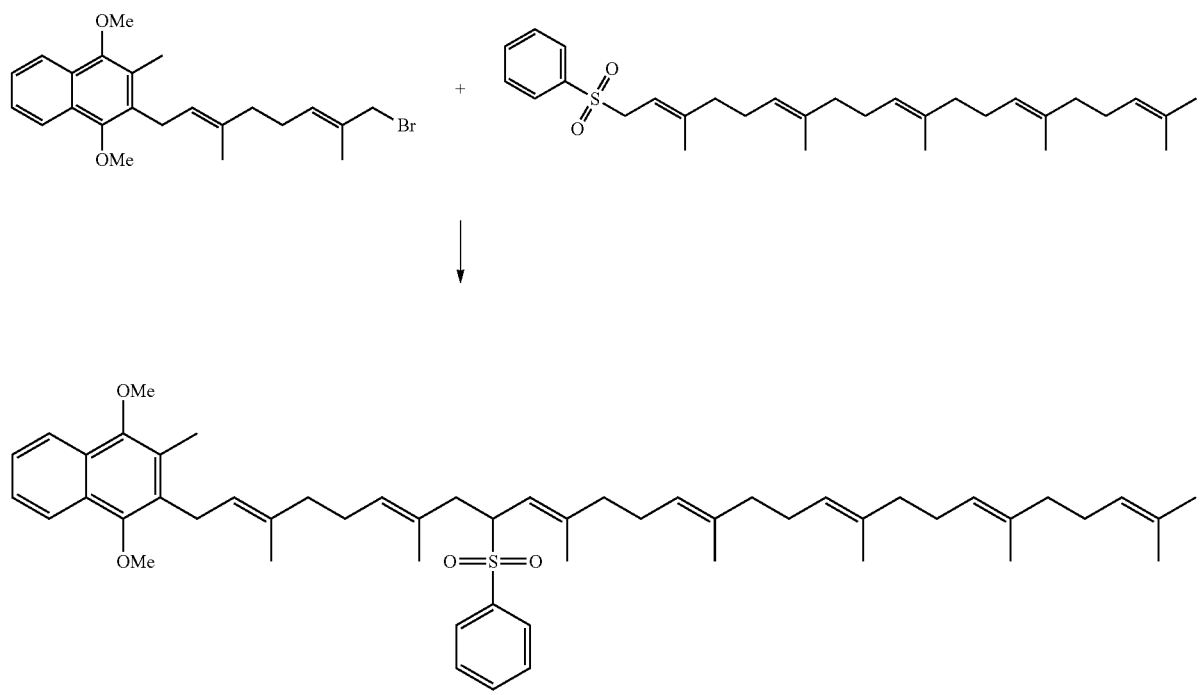

Scheme 7

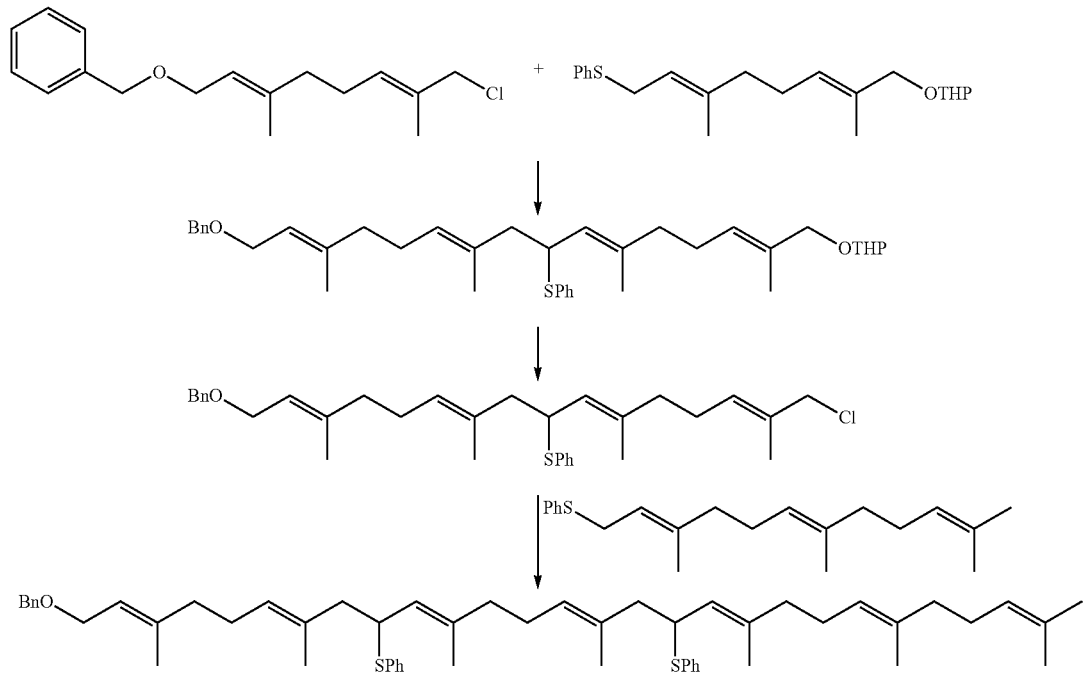

This "double Biellmann" chemistry forms a further aspect of the invention. Thus, viewed from a further aspect the invention provides a process for the preparation of a compound comprising an isoprenoid repeating unit comprising (i) reacting a compound of formula

with a compound

Where PG is a protecting group and n, LG and X are as hereinbefore defined to form

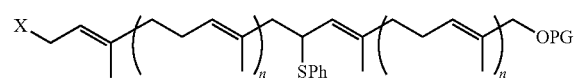

(ii) converting said OPG group into a leaving group and reacting with a compound

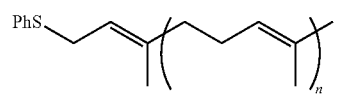

so as to form

(iii) and optionally reducing said SPh groups to hydride.

The inventors have also found however, that the Biellmann reaction can be carried out on a molecule in which the naphthoquinone ring (or a protected analogue thereof) is present. It may be therefore that the phenylthioether required in the Biellmann reaction already carries a naphthoquinone group. In scheme 8, after an initial Kumada coupling reaction, the side chain terminus is converted to a hydroxyl using selenium dioxide and this hydroxyl can be converted to a halide and coupled with phenythio or phenylsulfonyl substituted derivatives using chemistry described above.

Scheme 8a
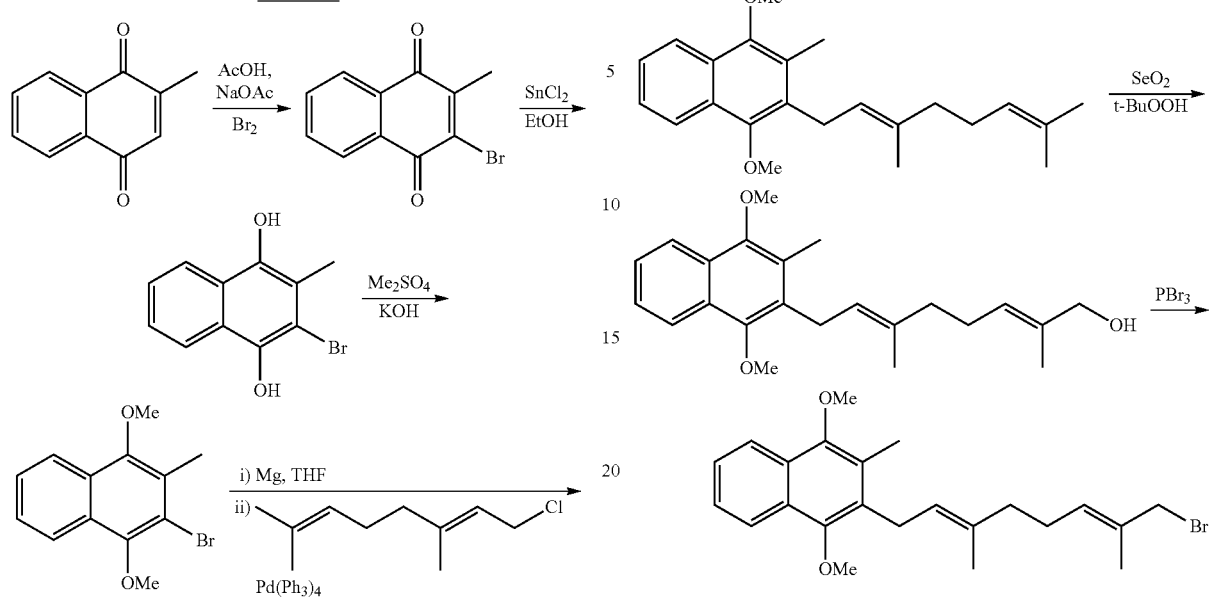
Scheme 8b
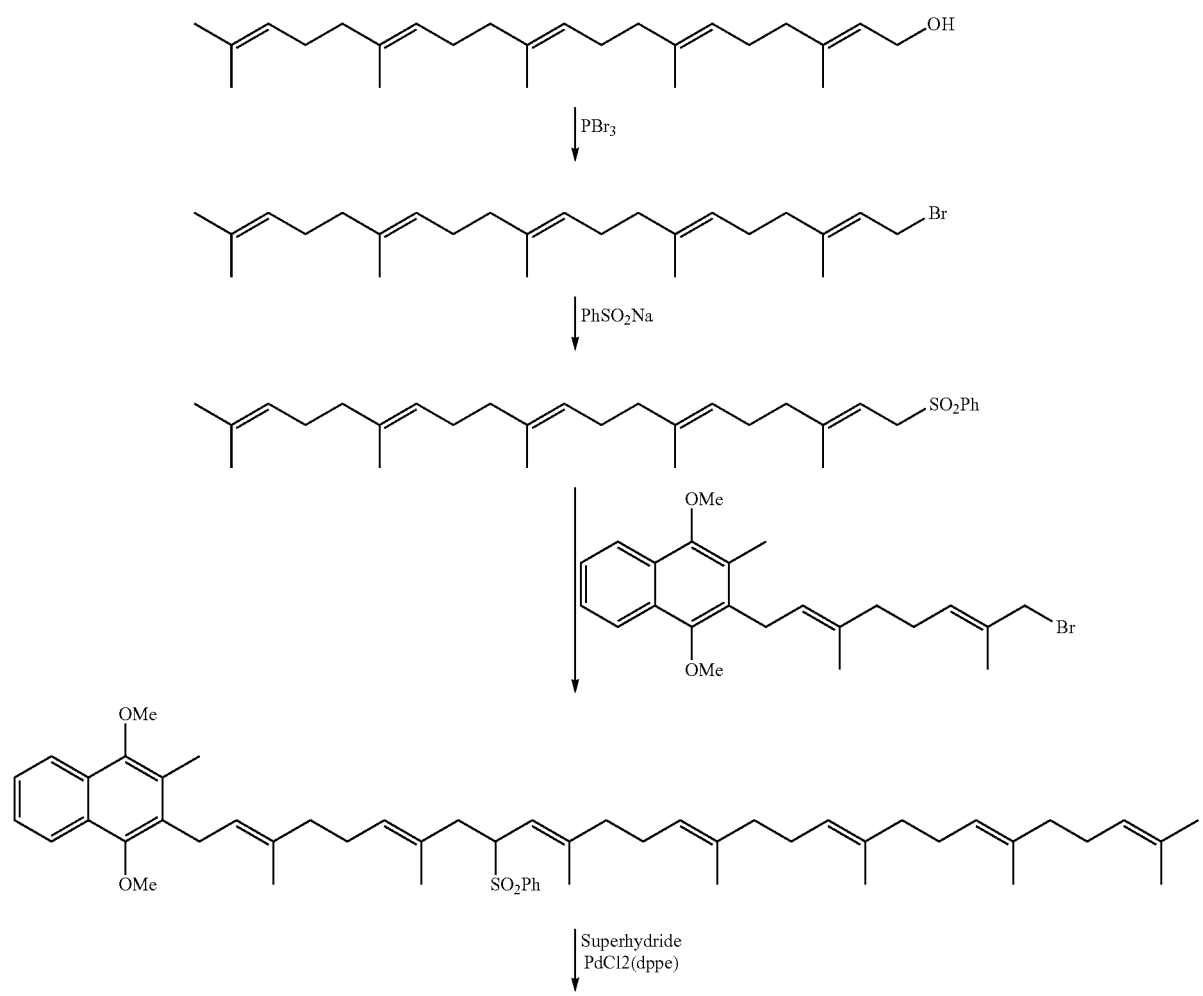

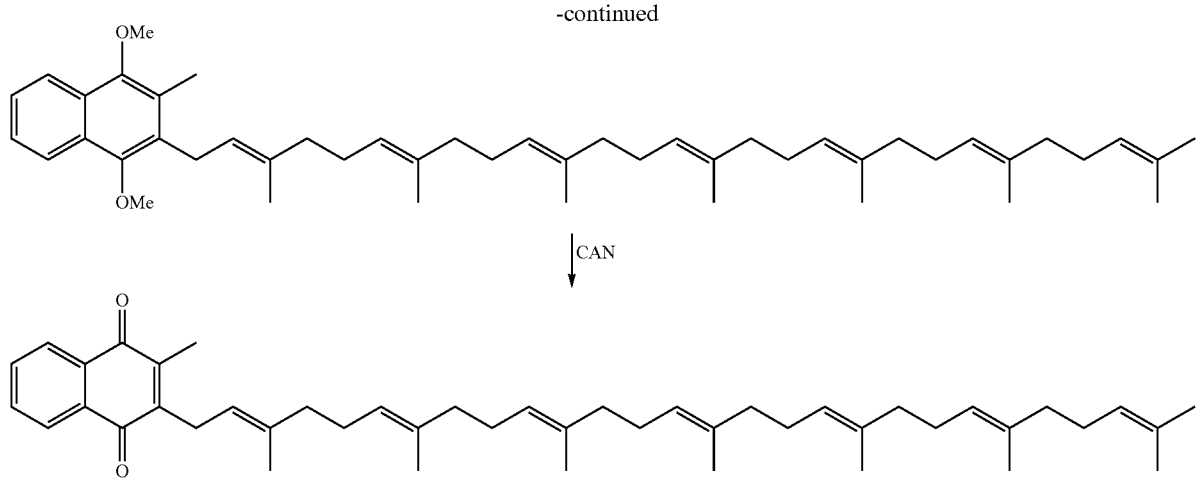

Conversion of the hydroxyl into phenythio or phenylsulfonyl group using the chemistry above gives an intermediate which can itself partake in a Biellmann coupling reaction to form a menaquinone molecule upon suitable work up procedures. This forms a still yet further aspect of the invention.

Thus, viewed from a further aspect the invention provides a process for the preparation of a compound of formula (I) as hereinbefore defined (I)

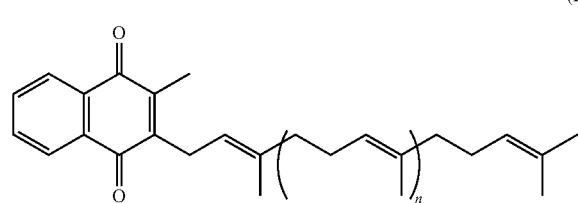

comprising (i) reacting a compound of formula (II) or (IV) with a compound of formula (III) in the presence of a copper, nickel or palladium catalyst;

(ii) converting X into a phenythio or phenylsulfonyl group to form compound (VII)

(VII)

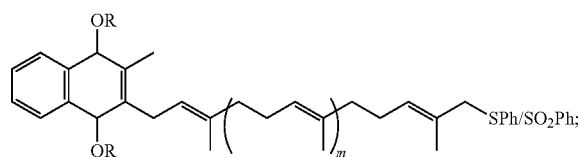

(iii) deprotonating (alpha to the sulphur) and reacting with a compound

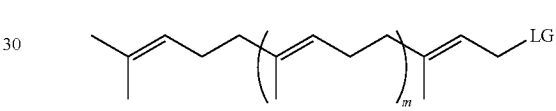

where m is independently as hereinbefore defined;

(iv) reductively removing the phenythio or phenylsulfonyl groups; and (v) converting by oxidation the diprotected naphthoquinone into a naphthoquinone.

This reaction can also be carried out using other R groups to protect the naphthoquinone and again it will be appreciated that the sum of the various n values of the starting materials will add up to the value of n in the compound of formula (I) taking into account any units formed in the reactions.

Certain key intermediates in the above reactions are also new and form a further aspect of the invention. These include the compounds:

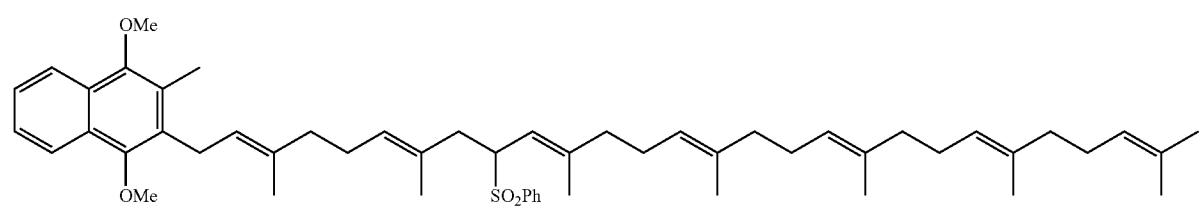

and

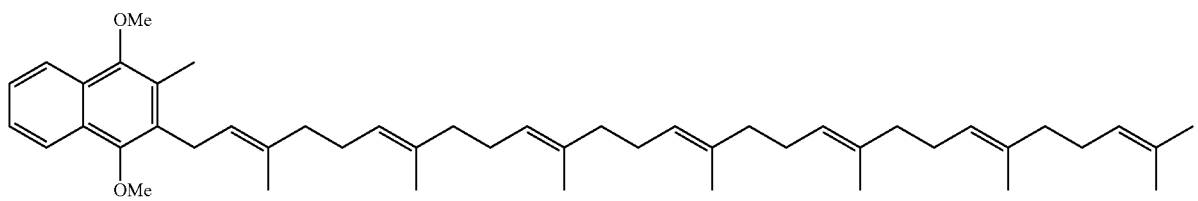

By varying the number of isoprenoid units in either molecule coupled using the Biellmann reaction, Suzuki coupling or Kumada coupling all manner of different menaquinone compounds can be produced.

The inventors have also devised alternative routes to compounds useful in such Biellman coupling reactions to form higher menaquinones. The inventors have devised an alternative process for the manufacture of these compounds in which the naphthoquinone ring is itself synthesised. The chemistry is based on that described by Tso et al in J Chem Res 1995, 104-105. The technique involves the reaction of a isoprenyl derivative in which the hydroxyl group is converted to an appropriate leaving group such as tosylate and reacted with $CH_2CHCH_2SO_2Ph$ in base. The base deprotonates the $CH_2CHCH_2SO_2Ph$ compound alpha to the sulphur and this can act as a nucleophile.

This can then be reacted with the benzolactone shown below to form the methylated naphthoquinone ring structure.

Scheme 9

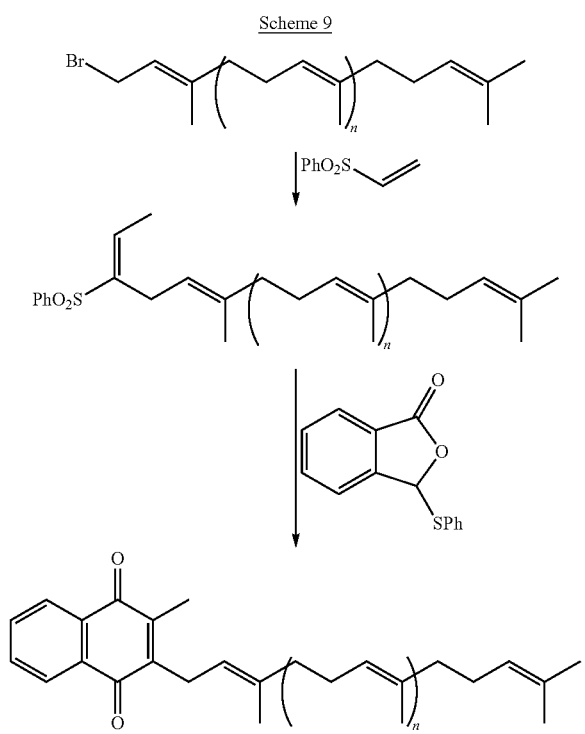

Treatment of this compound with selenium dioxide adds a terminal hydroxyl group which can be converted to a halide and then partake in further chemistry, e.g. in a Kumada type coupling to add further isoprenoid units to the side chain.

Thus viewed from a sixth aspect the invention provides a process for the preparation of a compound of formula (I) wherein

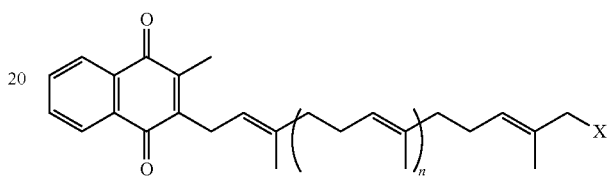

Comprising reacting a compound

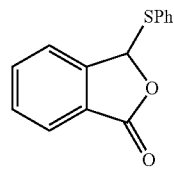

with

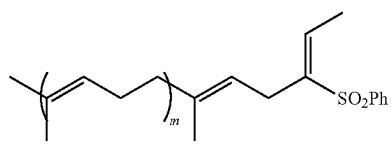

where m is as hereinbefore defined.

Throughout the processes above, it may be necessary to use different solvents and controlled reaction conditions. This is all well within the skills of the artisan. Typical solvents of use in the processes of the invention include, THF, DCM, DMSO, ethyl acetate, alcohols, amines, ethers, hydrocarbons, aryl solvents and so on. Where reactions need to be cooled, ice baths, dry ice baths or cooling machines can be used, for example.

The final products of the formula (1) formed by the processes of the invention are generally known compounds and have well documented therapeutic applications. The formed compounds may therefore be formulated as pharmaceutically acceptable compositions. The compounds of formula (I) have utility in the treatment of osteoporosis, cancer or cardio-vascular disease. The compounds may also be used as vitamin supplements or in any other known application of vitamin K, e.g. for injection into new-born infants to aid blood clotting.

It is a particular feature of the invention that the MK products achieved are highly pure. They have excellent stereochemical integrity and can be manufactured as solids as opposed to oils. In particular, the MK-n compounds manufactured according to the invention can be crystalline, especially crystalline MK-7.

In the schemes above, specific reaction conditions and reagents are disclosed to aid the skilled man in carrying out the reactions claimed. The chemistry could however be carried out under different conditions and using various reagents and the skilled man is aware of this. The reactions disclosed in the schemes are therefore disclosed per se and should not be considered as being limited to the use of the particular reagents mentioned in those schemes. The reactions in the schemes are disclosed irrespective of how each reaction is accomplished as well as in conjunction with the specific reagents mentioned.

The invention will now be further described with reference to the following non limiting examples:

Example 1

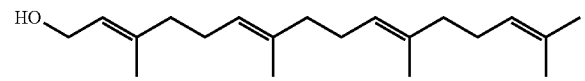 [SMILES: CC(C)=CCC/C(C)=C/CC/C(C)=C/CC/C(C)=C/CO]

(E,E,E)-Geranylgeraniol was prepared according to the literature (Jin, Y., Roberts, F. G and Coates, R. M., *Org. Synth.* (2007), 84, 43.

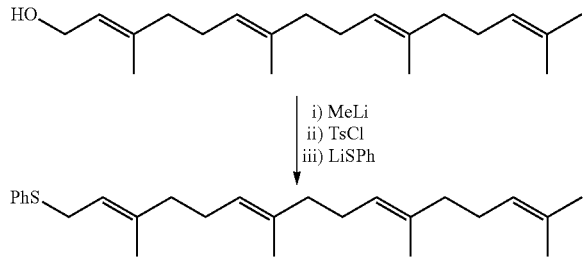

To a solution of (E,E,E)-geranylgeraniol (1.45 g, 5.00 mmol) in 3:1 dry ether/HMPA was added methyllitium (3.3 ml, 1.6 M in ether, 5.2 mmol) at 0° C. under nitrogen followed by p-toluenesulfonyl chloride (1.11 g, 5.82 mmol). After 2 hours at 0° C. lithium thiophenoxide (5.76 mmol, prepared from thiophenol and n-BuLi in THF) was added. The reaction mixture was allowed to reach room temperature and stirred for 2 hours. Water was added and the aqueous phase extracted with heptane (×3). The combined organic extract was washed with NaHCO$_3$ (aq) and brine, dried (Na$_2$SO$_4$), filtered and concentrated. The residue was purified by flash chromatography (heptane:EtOAc 95:5) to give 1.42 g (74%) of the product.

Example 2

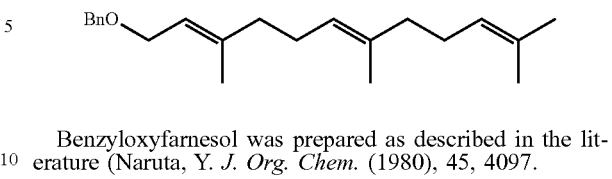

Benzyloxyfarnesol was prepared as described in the literature (Naruta, Y. *J. Org. Chem.* (1980), 45, 4097.

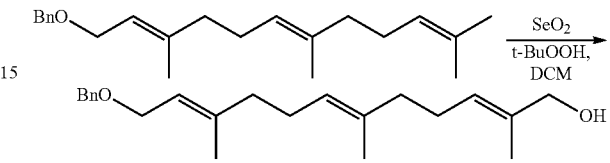

To a solution of benzyloxyfarnesol (50.0 g, 0.16 mol) in DCM (200 ml) was added SeO$_2$ (1.00 g, 9.01 mmol) and salicylic acid (2.24 g, 16.2 mmol) followed by t-BuOOH (67 ml, 80% in di t-butylperoxide:H$_2$O) at room temperature. The reaction mixture was stirred for 3.5 hours, silicagel added and the reaction mixture concentrated and purified directly by flash chromatography (heptane:EtOAc 7:1-4:1 gradient) to give 21.7 g (41%) as a colorless oil.

Example 3

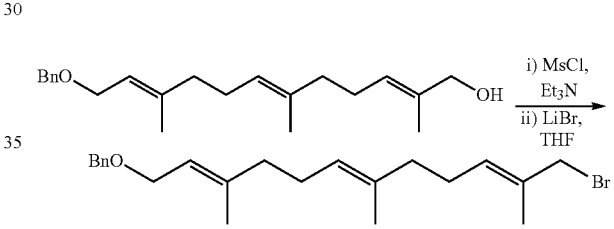

To a solution of the product from above (21.7 g, 66.0 mmol) in dry THF (220 ml) at −45° C. under argon was added slowly methanesulfonyl chloride (9.75 g, 85.1 mmol), followed by triethylamine (13.3 g, 131 mmol). The thus obtained white suspension was stirred at −45° C. for 45 min. A solution of lithium bromide (22.9 g, 264 mmol) in dry THF (75 ml) was added slowly. The dry ice/acetonitrile bath was replaced by an ice-bath and stirring continued for 1.5 hrs. The reaction mixture was poured into ice-water (600 ml) and the aqueous layer separated and extracted with ether (3×300 ml). The combined organic extracts were washed with ice-cold NaHCO$_3$ (400 ml) and brine (400 ml), dried (Na$_2$SO$_4$), filtered and concentrated to give 25.47 g (98%) of the product as a colorless oil used directly in the next step.

Example 4

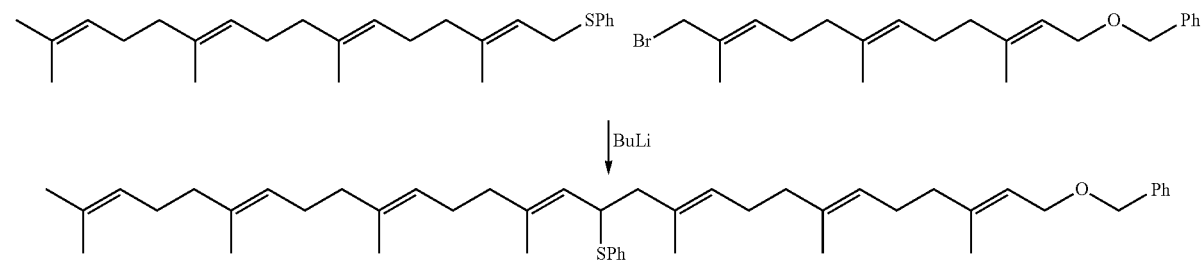

(E,E,E)-geranylgeraniol thiophenyl ether (2.11 g, 5.51 mmol) was dissolved in dry THF (35 ml), cooled to −78° C. and butyllithium added with stirring. The thus obtained bright yellow reaction mixture was stirred at −78° C. for 2.5 hrs under nitrogen. The product from the above reaction (1.78 g, 4.54 mmol) in dry THF (10 ml) was added and stirring continued at −78° C. for another 1.5 hrs. 4 ml 1:1 MeOH/ether was added and the reaction mixture allowed to reach room temperature at which point equal amounts of water and ether were added. The aqueous phase was extracted with ether (×3) and the combined extracts washed with brine, dried (Na$_2$SO$_4$), filtered and concentrated. Flash chromatography (heptane:EtOAc gradient) afforded 2.50 g (80%) of the product as a colourless oil.

Example 5

Example 6

2-Bromo-1,4-dimethoxy-3-methyl naphthalene was prepared by a modification of a method described in the literature (Adams, R., Geissman, B. R., Baker, B. R., Teeter, H. M. *JACS* (1941) 61, 528.)

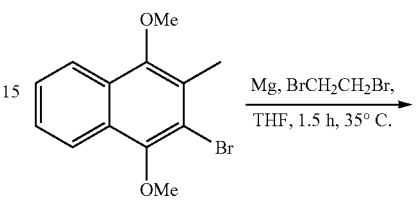

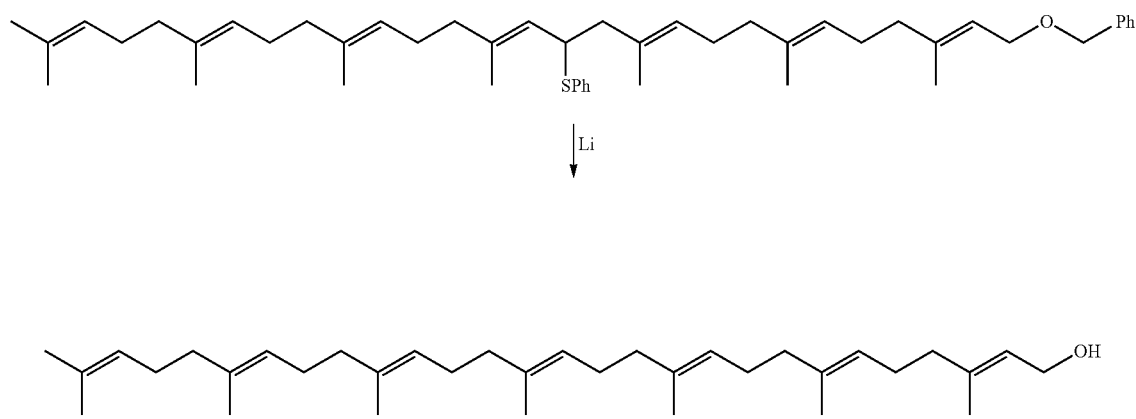

Under argon a reaction flask was charged with ethylamine (300 ml) at −78° C. Lithium (3.30 g, 476 mmol) in small pieces was added and the temperature raised to 0° C. for 45 min. The dark blue solution was cooled to −78° C. and a solution of the product from above (7.50 g, 10.8 mmol) in dry THF (60 ml) was added. After TLC showed complete conversion, 3-hexyne was added until complete dissipation of the blue colour. Methanol was added slowly until the reaction mixture became colourless. The reaction mixture was subsequently poured into ice-water and the aqueous phases extracted with ether (×3). The combined organic extract was washed with water, brine, dried (Na$_2$SO$_4$), filtered and concentrated. Flash chromatography (heptane: EtOAc 80:20) afforded 4.20 g (78%) product as a pale yellow oil.

Heptaprenol was converted to heptaprenyl bromide as described above or by applying PBr$_3$ in DCM or ether.

-continued

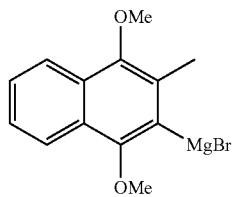

0.37 g (15.3 mmol) magnesium turnings were covered with dry THF and 30 □l 1,2-dibromoethane was added via septum and syringe. The mixture stood for 30 min. 1.43 g (5.08 mmol) 2-bromo-1,4-dimethoxy-3-methyl naphthalene dissolved in 3 ml of dry THF was added drop wise to the magnesium turnings over 30 min. The reaction mixture was cooled with a water bath, when it started to reflux. After that, the mixture was stirred at 35° C. for 1.5 hrs in a water bath until TLC showed complete conversion. The Grignard solution was used for the next step.

Example 7

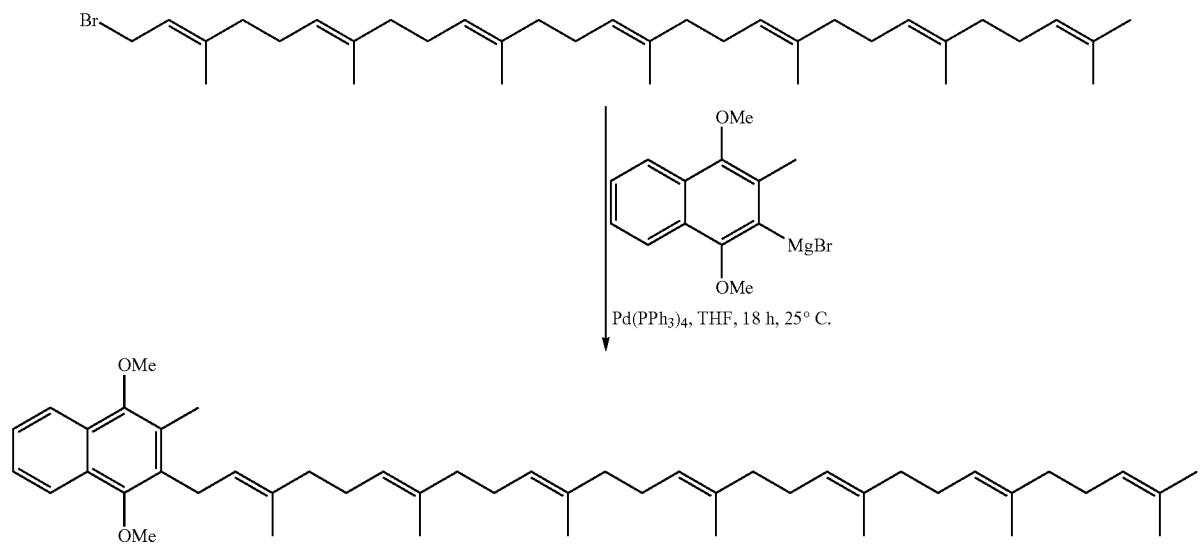

To heptaprenyl bromide (2.83 g, 5.08 mmol) dissolved in 5 ml of dry THF was added Pd(Ph$_3$)$_4$ (200 mg). To this yellow suspension, Grignard solution was added portion wise at room temperature after 5 min. The mixture was stirred over night. The reaction was quenched at room temperature by addition of NH$_4$Cl, the layers were separated and the aqueous layer was extracted with Et$_2$O. The combined organic extracts were dried over Na$_2$SO$_4$, filtered and concentrated in vacuo. The crude product was filtered through a short plug of silica gel to give 3.45 g of a pale yellow oil used directly in the final step.

Example 8

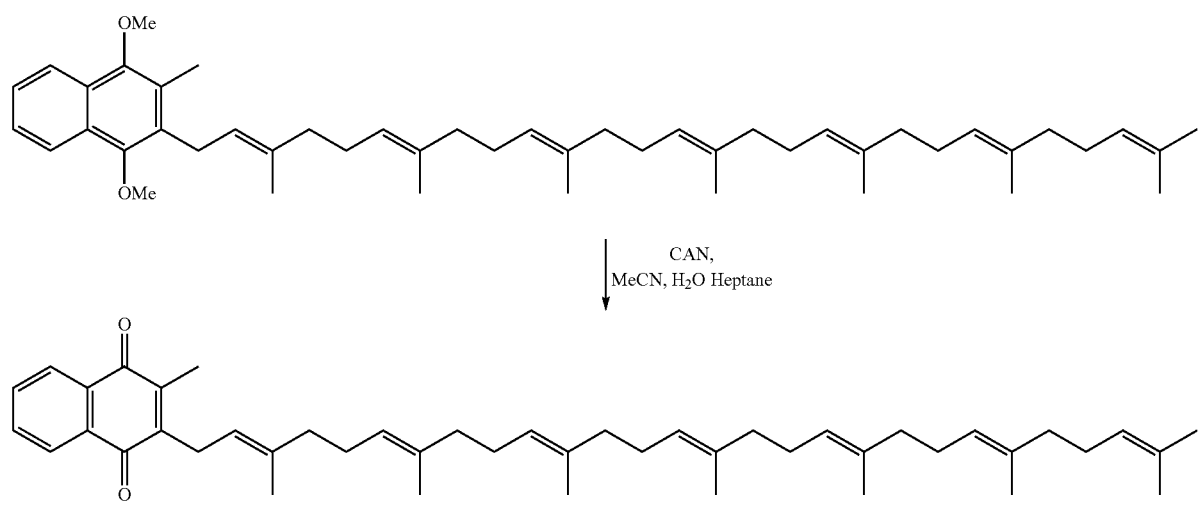

2-(3,7,11,15,19,23,27-heptamethyl-octacosa-2,6,10,14,18,22,26-heptaenyl)-1,4-dimethoxy-3-methyl-naphtalene (3.45 g, 5.08 mmol) was suspended in 10 ml of acetonitrile, 10 ml of heptane and 10 ml of H$_2$O and the suspension was cooled to 0° C. with an ice bath. At 0° C., CAN (7.00 g, 12.77 mmol) was added portion wise. The orange mixture was stirred at 0° C. for 30 min. and at room temperature for 30 min. The yellow mixture was poured into 100 ml ice water. The layers were separated and the aqueous layer was extracted with EtOAc (x3). The combined organic extracts were washed with brine, dried over Na$_2$SO$_4$, filtered and concentrated. Flash chromatography (heptane:EtOAc 99:1-97.5:2.5-95:5) afforded 1.83 g (56%) of the product.

$^1$H NMR (200 MHz, CDCl$_3$) δ 8.07-8.00 (m, 2H), 7.69-7.63 (m, 2H), 5.08-4.97 (m, 7H), 3.35 (d, $^3$J=6.9 Hz, 2H) 2.16 (s, 3H), 2.05-1.81 (m, 24H), 1.77 (s, 3H), 1.65 (s, 3H), 1.57 (s, 12H), 1.54 (s, 6H); $^{13}$C NMR (50 MHz, CDCl$_3$) δ 185.34, 184.40, 146.08, 143.27, 137.48, 135.15, 134.84, 133.25, 133.19, 132.13, 132.09, 131.15, 126.24, 126.13, 124.37, 124.23, 124.11, 123.80, 119.05, 39.68, 26.72, 26.65, 26.45, 25.96, 25.65, 17.63, 16.38, 15.97, 12.62

Example 9

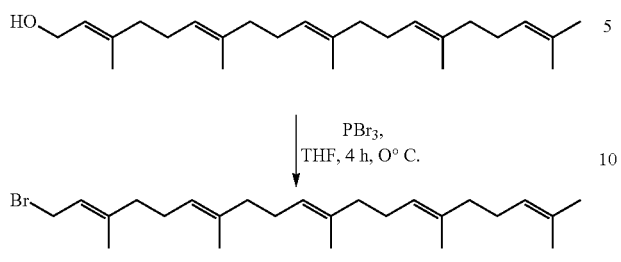

10.83 g (30.20 mmol) 3,7,11,15,19-pentamethyl-eicosa-2,6,10,14,18-pentaen-1-ol was dissolved in 60 ml of dry THF. At 0° C., 1.5 ml (4.32 g, 15.96 mmol) PBr$_3$ were added drop wise via septum and syringe and the clear, colourless solution was stirred at 0° C. for 4 h. The reaction was quenched by addition of ice cold water. The layers were separated and the aqueous layer was extracted with ether. The combined organic extracts were washed with NaHCO$_3$ and brine, dried over Na$_2$SO$_4$, filtered and concentrated in vacuo to give 1-bromo-3,7,11,15,19-pentamethyl-eicosa-2,6,10,14,18-pentaene as a colourless oil (10.89 g, 25.84 mmol, 86%). The crude product was used for the next step without further purification.

Example 10

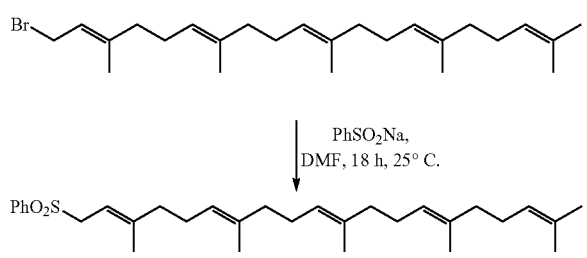

10.89 g (25.84 mmol) allylic bromide was dissolved in 200 ml of DMF and 21.30 g (129.75 mmol) benzene sulfinic acid sodium salt was added in one portion at room temperature. The suspension was stirred at room temperature for 18 h over night. The mixture was poured into ice water. The layers were separated and the aqueous layer was extracted with EtOAc. The combined organic extracts were washed with ice water and ice cold brine, dried over Na$_2$SO$_4$, filtered and concentrated in vacuo by rotary evaporation at 40° C. The residue was purified by dry flash. A gradient heptane:EtOAc (90:10) to heptane:EtOAc (70:30) was used as eluent to afford 6.14 g (12.71 mmol, 50%) of pure (3,7,11,15,19-pentamethyl-eicosa-2,6,10,14,18-pentaene-1-sulfonyl)-benzene (as colourless oil and 2.92 g (6.05 mmol, 24%) of mixed fractions containing mostly (3,7,11,15,19-pentamethyl-eicosa-2,6,10,14,18-pentaene-1-sulfonyl)-benzene as colourless oil.

$^1$H NMR (200 MHz, CDCl$_3$) δ 7.86-7.81 (m, 2H), 7.60-7.45 (m, 3H), 5.20-5.04 (m, 5H), 3.77 (d, $^3$J=8.0 Hz, 2H), 2.05-1.87 (m, 16H), 1.65 (s, 3H), 1.56 (s, 12H), 1.27 (s, 3H); $^{13}$C NMR (50 MHz, CDCl$_3$) δ 146.33, 138.60, 135.65, 134.94, 134.80, 133.42, 131.13, 128.85, 128.48, 124.32, 124.15, 124.03, 123.24, 124.37, 110.23, 56.01, 39.63, 31.80, 26.68, 26.57, 26.11, 25.62, 22.61, 17.60, 16.09, 15.93, 14.04.

Example 11

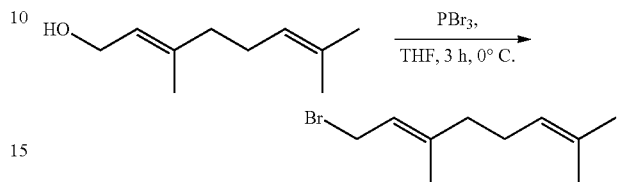

10.02 g (64.96 mmol) geraniol was dissolved in 120 ml of dry THF. At 0° C., 3.1 ml (8.93 g, 32.98 mmol) PBr$_3$ were added drop wise via septum and syringe and the clear, colorless solution was stirred at 0° C. for 3 h. The reaction was quenched by addition of ice cold water. The layers were separated and the aqueous layer was extracted with ether. The combined organic extracts were washed with NaHCO$_3$ and brine, dried over Na$_2$SO$_4$, filtered and concentrated in vacuo to give geranyl bromide as a colourless oil (13.59 g, 62.63 mmol, 96%). The crude product was used for the next step without further purification.

Example 12

2-Bromo-1,4-dimethoxy-3-methyl naphthalene was prepared by a modification of a method described in the literature (Adams, R., Geissman, B. R., Baker, B. R., Teeter, H. M. *JACS* (1941) 61, 528.)

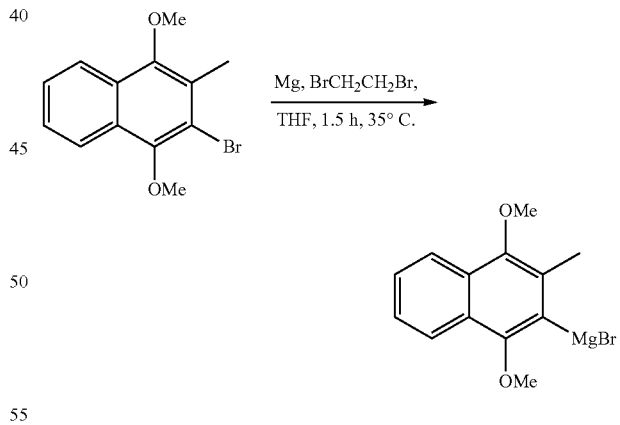

4.68 g (195 mmol) magnesium turnings were covered with dry THF and 0.5 ml (1.09 g, 5.80 mmol) 1,2-dibromo ethane was added via septum and syringe. The mixture stood for 30 min. 18.37 g (65.37 mmol) 2-bromo-1,4-dimethoxy-3-methyl naphthalene dissolved in 30 ml of dry THF was added drop wise to the magnesium turnings over 30 min. The reaction mixture was cooled with a water bath, when it started to reflux. After that, the mixture was stirred at 35° C. for 1.5 h in a water bath until TLC showed complete conversion. The Grignard solution was used for the next step.

Example 13

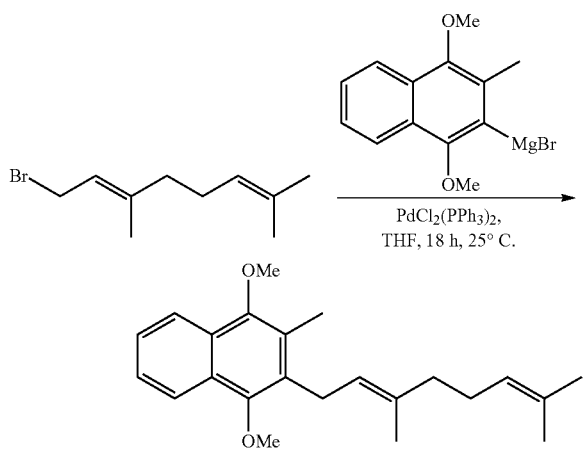

13.59 g (62.63 mmol) geranyl bromide dissolved in 100 ml of dry THF was added to 0.91 g (1.297 mmol) PdCl$_2$(PPh$_3$)$_2$. To this yellow suspension, Grignard solution was added portion wise at room temperature. The mixture was stirred over night for 18 h. The reaction was quenched at room temperature by addition of NH$_4$Cl, the layers were separated and the aqueous layer was extracted with Et$_2$O. The combined organic extracts were dried over Na$_2$SO$_4$, filtered and concentrated in vacuo to give 23.44 g of a brown oil. The residue was dissolved in little CH$_2$Cl$_2$ and was filtered through a plug of SiO$_2$ (50-60 g) to remove palladium residues. The plug was washed with CH$_2$Cl$_2$ until all product was washed out (checked by TLC). The combined fractions were concentrated in vacuo. The crude product 2-(3,7-dimethyl-octa-2,6-dienyl)-1,4-dimethoxy-3-methyl-naphtalene was used in the next step without further purification.

$^1$H NMR (200 MHz, CDCl$_3$) δ 8.07-8.03 (m, 2H), 7.47-7.42 (m, 2H), 5.13-5.07 (m, 2H), 3.88 (s, 3H), 3.86 (s, 3H), 3.56 (d, $^3$J=6.1 Hz, 2H), 2.37 (s, 3H), 2.03 (m, 4H), 1.82 (s, 3H), 1.63 (s, 3H), 1.56 (s, 3H); $^{13}$C NMR (50 MHz, CDCl$_3$) δ 150.07, 149.71, 135.63, 131.37, 130.91, 127.46, 127.24, 126.93, 125.36, 125.23, 124.20, 122.90, 122.25, 122.08, 62.15, 61.28, 39.63, 26.53, 26.31, 25.65, 17.64, 16.32, 12.32

Example 14

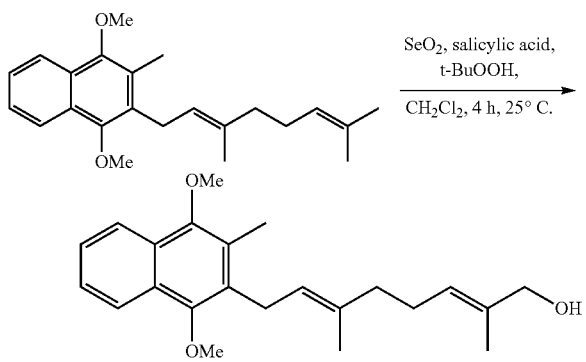

0.37 g (3.34 mmol) SeO$_2$, 0.94 g (6.81 mmol) salicylic acid and 23 ml of t-BuOOH (70 wt % in water) were suspended in 85 ml of CH$_2$Cl$_2$. The suspension was stirred at room temperature for 40 min and then cooled to 0° C. with an ice bath. At 0° C., 21.08 g (62.37 mmol) crude 2-(3,7-dimethyl-octa-2,6-dienyl)-1,4-dimethoxy-3-methyl-naphtalene dissolved in 45 ml of CH$_2$Cl$_2$ was added in one portion. After stirring at 0° C. for 5 h the suspension was diluted with 150 ml of toluene and the solvent was removed in vacuo by rotary evaporation at 40° C. The residue was taken up in 150 ml of CH$_2$Cl$_2$ and the red brown solution was washed with NaHCO$_3$, dried over Na$_2$SO$_4$, filtered and concentrated in vacuo by rotary evaporation at 30° C. The residue was dissolved in 140 ml of dry THF and 7 ml of MeOH, cooled to 0° C. with an ice bath and 2.44 g (64.50 mmol) NaBH$_4$ was added portion wise. The mixture was stirred at 0° C. for 30 min and 50 ml of ice cold saturated NH$_4$Cl was added portion wise at 0° C. to quench the reaction. The layers were separated and the aqueous layer was extracted with Et$_2$O. The combined organic extracts were washed with brine, dried over Na$_2$SO$_4$, filtered and concentrated in vacuo by rotary evaporation at 30° C. to give a dark brown oil (21.48 g). The residue was purified by dry flash. A gradient heptane:EtOAc (80:20) to heptane:EtOAc (60:40) was used as eluent to afford 6.43 g (18.17 mmol, 28% over 3 steps from geraniol) of 8-(1,4-dimethoxy-3-methyl-napthalen-2-yl)-2,6-dimethyl-octa-2,6-dien-1-ol as a oil.

$^1$H NMR (200 MHz, CDCl$_3$) δ 8.06-8.01 (m, 2H), 7.48-7.40 (m, 2H), 5.34-5.28 (m, 1H), 5.12-5.05 (m, 1H), 3.92 (m, 2H), 3.86 (s, 3H), 3.54 (d, $^3$J=5.9 Hz, 2H), 2.36 (s, 3H), 2.14-2.03 (m, 4H), 1.70 (s, 3H), 1.61 (s, 3H).

Example 15

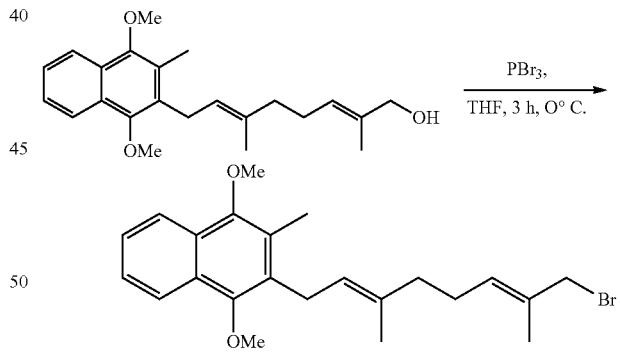

6.45 g (18.22 mmol) of 8-(1,4-dimethoxy-3-methyl-napthalen-2-yl)-2,6-dimethyl-octa-2,6-dien-1-ol was dissolved in 45 ml of dry THF. At 0° C., 0.9 ml (2.59 g, 9.58 mmol) PBr$_3$ was added drop wise via septum and syringe and the clear, colourless solution was stirred at 0° C. for 3 h. The reaction was quenched by addition of ice cold water. The layers were separated and the aqueous layer was extracted with ether. The combined organic extracts were washed with NaHCO$_3$ and brine, dried over Na$_2$SO$_4$, filtered and concentrated in vacuo to give 2-(8-bromo-3,7-dimethyl-octa-2,6-dienyl)-1,4-dimethoxy-3-methyl-naphtalene as a colorless oil (6.29 g, 15.08 mmol, 83%). The crude product was used for the next step without further purification.

Example 16

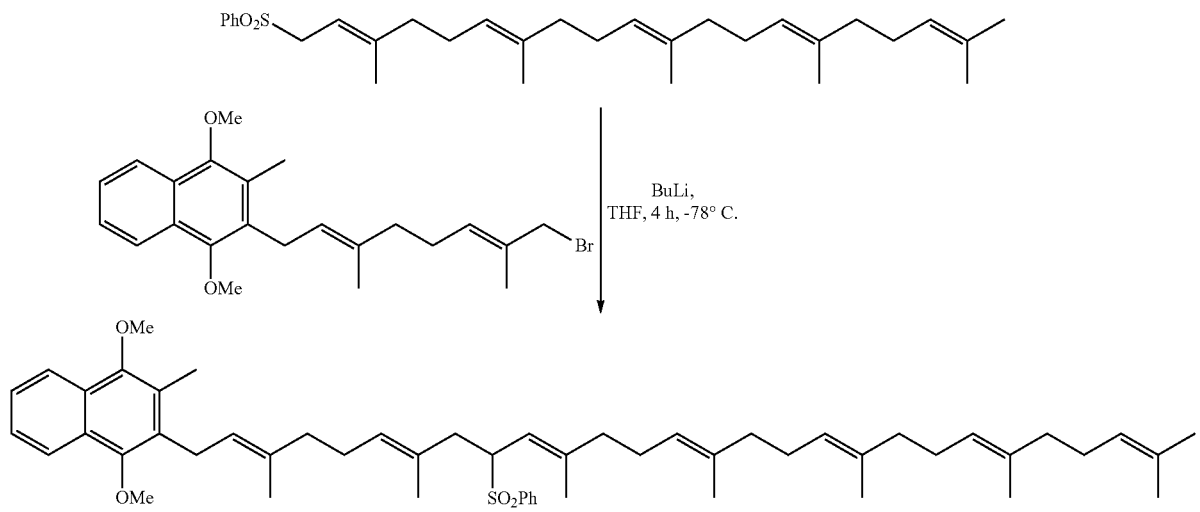

9.06 g (18.76 mmol) (3,7,11,15,19-pentamethyl-eicosa-2,6,10,14,18-pentaene-1-sulfonyl)-benzene were dissolved in 80 ml of dry THF and the solution was cooled to −78° C. with CO$_2$/MeOH. At −78° C., 11.80 ml (18.88 mmol) BuLi (1.6 M solution in hexane) was added drop wise via septum and syringe over 10 min. The orange solution was stirred for 2.5 h at −78° C. 6.07 g (14.56 mmol) 2-(8-bromo-3,7-dimethyl-octa-2,6-dienyl)-1,4-dimethoxy-3-methyl-naphtalene dissolved in 30 ml of dry THF was added via dropping funnel over 10 min. The brown reaction mixture was stirred at −78° C. for 1.5 h. At −78° C., the reaction was quenched by addition of 50 ml of a Et$_2$O/MeOH mixture (1:1 v/v). The mixture was allowed to reach room temperature and after that 100 ml of saturated NH$_4$Cl solution was added. The layers were separated and the aqueous layer was extracted with Et$_2$O. The combined organic extracts were washed with brine, dried over Na$_2$SO$_4$, filtered and concentrated in vacuo by rotary evaporation at 30° C. to give 16.21 g of 2-(9-benzenesulfonyl-3,7,11,15,19,23,27-heptamethyl-octacosa-2,6,10,14,18,22,26-heptaenyl)-1,4-dimethoxy-3-methyl-naphtalene as a brownish yellow oil, which was used in the next step without further purification.

Example 17

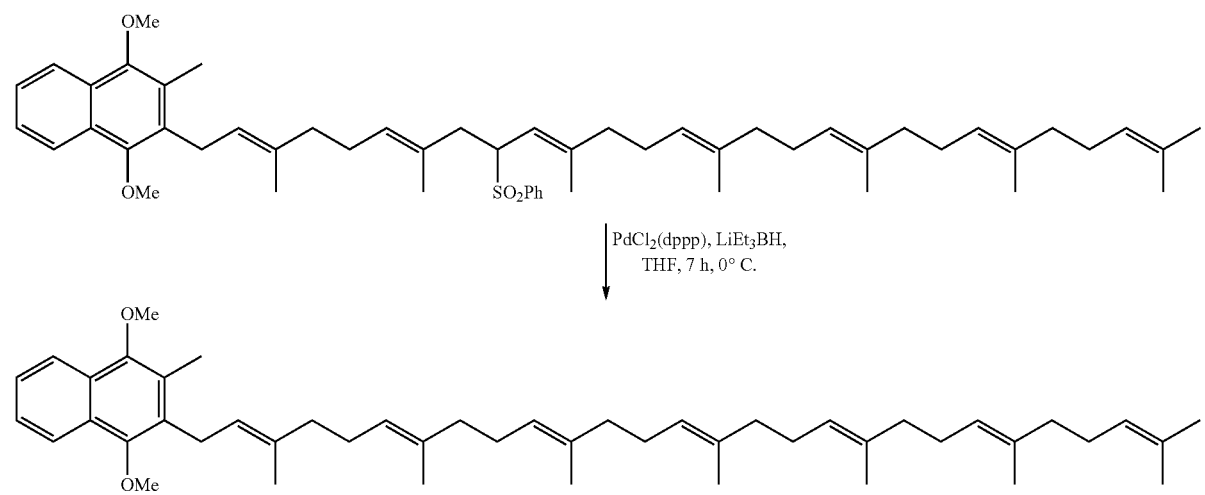

16.21 g 2-(9-benzenesulfonyl-3,7,11,15,19,23,27-heptamethyl-octacosa-2,6,10,14,18,22,26-heptaenyl)-1,4-dimethoxy-3-methyl-naphtalene mixture was dissolved in 120 ml of dry THF and 0.57 g (0.96 mmol) PdCl$_2$(dppp) was added in one portion and the suspension was cooled to 0° C. with an ice bath. At 0° C., 42.00 ml (42.00 mmol) LiEt$_3$BH (1.0 M solution in THF) were added portion wise via septum and syringe over 20 min. The dark brown solution was stirred at 0° C. for 7 h. At 0° C., the reaction was quenched by addition 100 ml of saturated NH$_4$Cl solution. The layers were separated and the aqueous layer was extracted with Et$_2$O.

The combined organic extracts were washed with saturated NH$_4$Cl solution, dried over Na$_2$SO$_4$, filtered and concentrated in vacuo by rotary evaporation at 30° C. to give 18.18 g of dark brown oil. It was purified by dry flash with $CH_2Cl_2$ as eluent to afford 11.01 g of yellow oil, which was used in the next step without further purification.

$^1H$ NMR (200 MHz, $CDCl_3$) δ 8.09-8.01 (m, 2H), 7.49-7.41 (m, 2H), 5.11-5.08 (m, 7H), 3.88 (s, 3H), 3.86 (s, 3H), 3.57 (d, $^3J$=6.3 Hz, 2H) 2.38 (s, 3H), 2.05-1.85 (m, 24H), 1.83 (s, 3H), 1.68 (s, 3H), 1.60 (s, 12H), 1.57 (s, 6H); $^{13}C$ NMR (50 MHz, $CDCl_3$) δ 150.07, 149.71, 135.71, 135.08, 134.92, 134.86, 127.46, 127.23, 126.89, 125.35, 125.23, 124.40, 124.25, 124.16, 124.01, 122.80, 122.25, 122.08, 62.14, 61.27, 39.71, 26.75, 26.65, 26.54, 26.31, 25.66, 17.66, 16.39, 15.99, 12.37

Example 18

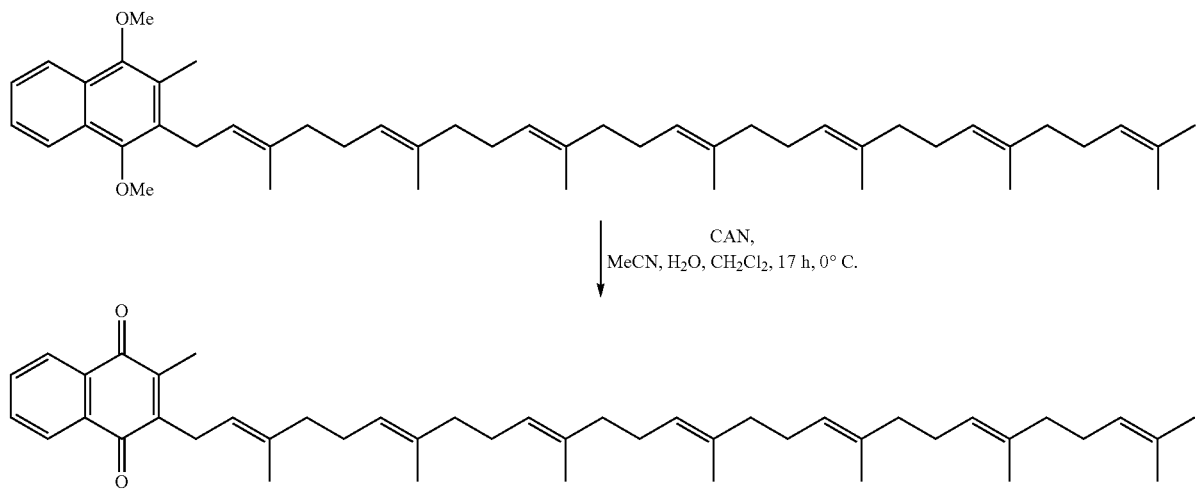

2-(3,7,11,15,19,23,27-heptamethyl-octacosa-2,6,10,14,18,22,26-heptaenyl)-1,4-dimethoxy-3-methyl-naphtalene (8.50 g, 12.54 mmol) was suspended in 45 ml of acetonitrile, 45 ml of $CH_2Cl_2$ and 20 ml of $H_2O$ and the suspension was cooled to 0° C. with an ice bath. At 0° C., an ice cold solution of 17.26 g (31.48 mmol) CAN in 32 ml of acetonitrile and 32 ml of $H_2O$ was added portion wise via dropping funnel over 20 min. The orange mixture was stirred at 0° C. for 40 min. and at room temperature for 16.5 h over night. The yellow mixture was poured into 100 ml ice water. The layers were separated and the aqueous layer was extracted with $CH_2Cl_2$. The combined organic extracts were washed with ice water, dried over $Na_2SO_4$, filtered and concentrated in vacuo by rotary evaporation at 40° C. to give 8.50 g of yellow oil.

It was purified by dry flash. A gradient heptane:EtOAc (100:1) to heptane:EtOAc (95:5) was used as eluent to afford 4.93 g (7.61 mmol, 42% over 4 steps from 2-(8-bromo-3,7-dimethyl-octa-2,6-dienyl)-1,4-dimethoxy-3-methyl-naphtalene) of brownish yellow oil, which solidified in the fridge and was recrystallized from EtOAc and ethanol to give 3.5 g of MK7 as a bright yellow solid.

$^1H$ NMR (200 MHz, $CDCl_3$) δ 8.07-8.00 (m, 2H), 7.69-7.63 (m, 2H), 5.08-4.97 (m, 7H), 3.35 (d, $^3J$=6.9 Hz, 2H) 2.16 (s, 3H), 2.05-1.81 (m, 24H), 1.77 (s, 3H), 1.65 (s, 3H), 1.57 (s, 12H), 1.54 (s, 6H); $^{13}C$ NMR (50 MHz, $CDCl_3$) δ 185.34, 184.40, 146.08, 143.27, 137.48, 135.15, 134.84, 133.25, 133.19, 132.13, 132.09, 131.15, 126.24, 126.13, 124.37, 124.23, 124.11, 123.80, 119.05, 39.68, 26.72, 26.65, 26.45, 25.96, 25.65, 17.63, 16.38, 15.97, 12.62

Example 19

The synthesis of allylic thioether from literature known compounds is outlined in Scheme A.

Scheme A: Synthesis of allylic thioether.

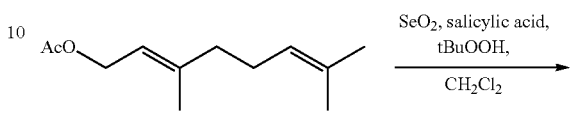

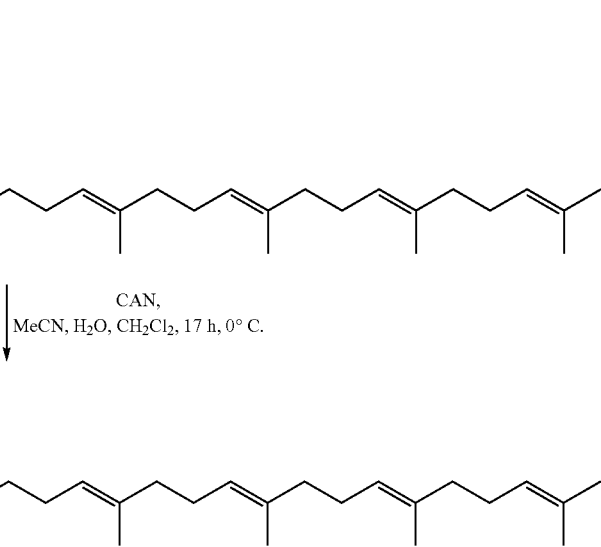

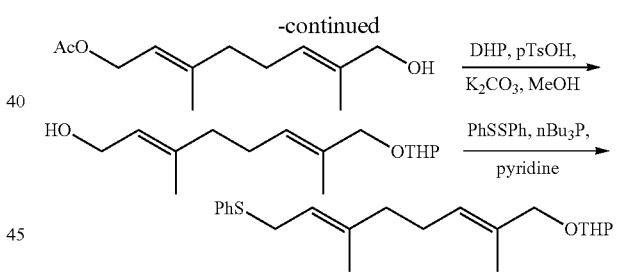

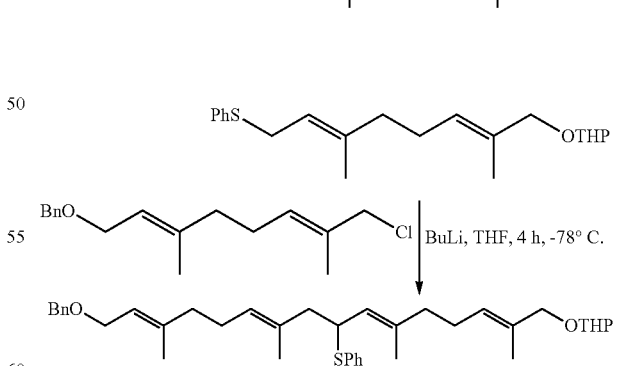

1.80 g (5.20 mmol) thioether was dissolved in 30 ml of dry THF. The solution was cooled to −78° C. with a $CO_2$/MeOH cooling bath and at −78° C.; 3.30 ml (5.28 mmol) BuLi (1.6 M solution in hexane) was added drop wise via septum and syringe. The clear, yellow orange solution was stirred at −78° C. for 2.5 h and then 1.20 g (4.32 mmol)

allylic chloride dissolved in 10 ml of dry THF was added drop wise via septum and syringe at −78° C. The clear solution was stirred at −78° C. for 1.5 h. At −78° C., 10 ml of a MeOH/Et₂O mixture (1:1 v/v) was added and the mixture was allowed to reach room temperature and then 35 ml of sat. NH₄Cl solution was added. The layers were separated and the aqueous layer was extracted with diethyl ether (3×40 ml). The organic layers were dried over Na₂SO₄, filtered and concentrated in vacuo by rotary evaporation at 30° C. to give 3.15 g of yellow oil. The crude product was further purified by flash column chromatography on SiO₂ using a mixture of heptane:EtOAc (9/1 v/v) as eluent to give a yellow oil (2.09 g, 3.56 mmol, 83%).

¹H NMR (200 MHz, CDCl₃) δ 7.42-7.21 (m, 10H), 5.39-5.34 (m, 2H), 5.16-5.14 (m, 1H), 5.01-4.96 (m, 1H), 4.57 (m, 1H), 4.49 (s, 2H), 4.11-3.77 (m, 6H), 3.59-3.41 (m, 1H), 2.35-1.70 (m, 12H), 1.63 (s, 6H), 1.58 (m, 3H), 1.34 (s, 3H)

Example 20

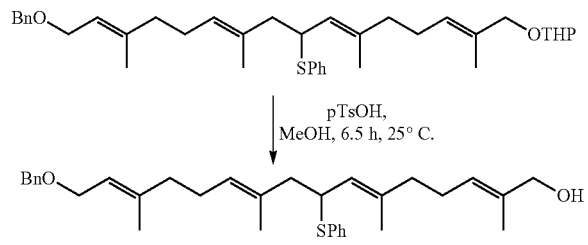

2.09 g (3.55 mmol) THP ether was dissolved in 25 ml of dry MeOH. 0.21 g (1.10 mmol) pTsOH monohydrate was added in one portion. The clear mixture was stirred at room temperature for 6.5 h. After that, the reaction mixture was concentrated in vacuo by rotary evaporation at 40° C. and the residue was dissolved in 50 ml of CH₂Cl₂ and washed with 50 ml of NaHCO₃ solution. The aqueous layer was extracted with CH₂Cl₂ (50 ml). The combined organic extracts washed with brine (50 ml), dried over Na₂SO₄, filtered and concentrated in vacuo by rotary evaporation at 30° C. to give 1.81 g of yellow oil. The crude product was further purified by flash column chromatography on SiO₂ using a mixture of heptane:EtOAc (60/40 v/v) as eluent to give a yellow oil (1.50 g, 2.98 mmol, 84%).

¹H NMR (200 MHz, CDCl₃) δ 7.40-7.18 (m, 10H), 5.37-5.28 (m, 2H), 5.14-5.13 (m, 1H), 5.00-4.94 (m, 1H), 4.48 (s, 2H), 4.06-3.92 (m, 5H), 2.34-1.90 (m, 10H), 1.62 (s, 6H), 1.56 (m, 3H), 1.36 (s, 3H)

Example 21

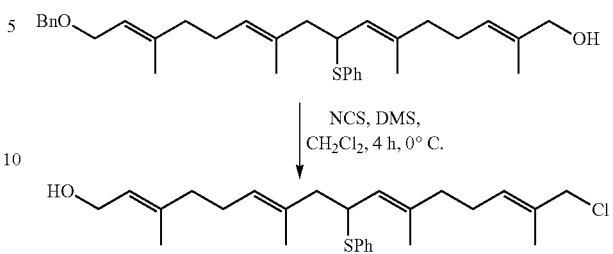

0.74 g (5.54 mmol) NCS were suspended in 20 ml of dry CH₂Cl₂. At 0° C., 0.55 ml (0.47 g, 7.41 mmol) DMS was added neat via syringe. The colourless suspension was stirred for 15 min. and then 1.5 g (2.98 mmol) allylic alcohol was added. The mixture was stirred at 0° C. for 4 h. The mixture was poured into 50 ml of ice cold brine. The layers were separated and the aqueous layer was extracted with heptane (2×50 ml). The combined organic extracts were diluted with 100 ml of heptane washed with brine (2×100 ml), dried over Na₂SO₄, filtered and concentrated in vacuo by rotary evaporation at 40° C. to give the product as a bright yellow oil (1.51 g, 2.89 mmol, 97%). The crude product was used in the next step without further purification.

¹H NMR (200 MHz, CDCl₃) δ 7.76-7.20 (m, 10H), 5.42-5.35 (m, 2H), 5.18-5.10 (m, 1H), 5.00-4.95 (m, 1H), 4.48 (s, 2H), 4.02-3.94 (m, 5H), 2.55-1.95 (m, 10H), 1.76-1.57 (m, 12H). CDCl₃ solvent peak: δ 7.24.

Example 22

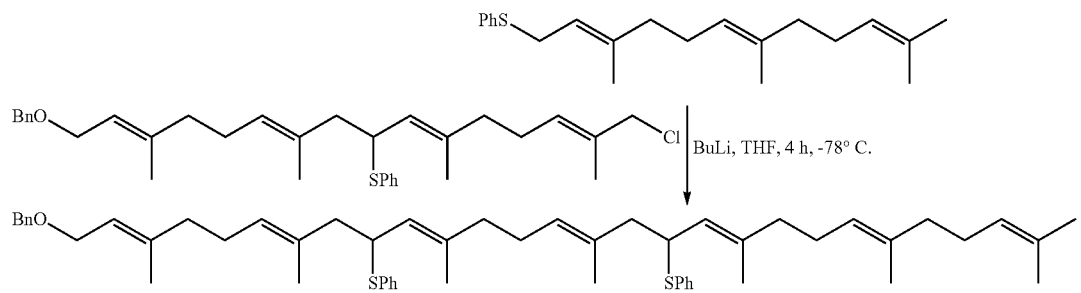

1.18 g (3.76 mmol) farnesol thiophenylether was dissolved in 20 ml of dry THF. The solution was cooled to −78° C. with a CO₂/MeOH cooling bath and at −78° C.; 2.30 ml (3.68 mmol) BuLi (1.6 M solution in hexane) was added drop wise via septum and syringe. The clear, yellow orange solution was stirred at −78° C. for 2.5 h and then 1.51 g (2.89 mmol) allylic chloride dissolved in 7 ml of dry THF was added drop wise via septum and syringe at −78° C. The clear solution was stirred at −78° C. for 1.5 h. At −78° C., 18 ml of a MeOH/Et₂O mixture (1:1 v/v) was added and the mixture was allowed to reach room temperature and then 30 ml of sat. NH₄Cl solution was added. The layers were separated and the aqueous layer was extracted with diethyl ether (3×30 ml). The organic layers were dried over Na₂SO₄, filtered and concentrated in vacuo by rotary evaporation at 30° C. to give 2.64 g of yellow oil. The crude product was further purified by flash column chromatography on SiO₂ using a mixture of heptane:EtOAc (9/1 v/v) as eluent to give a yellow oil (1.55 g, 1.93 mmol, 67%).

$^1$H NMR (200 MHz, CDCl$_3$) δ 7.55-7.20 (m, 15H), 5.42-5.35 (m, 1H), 5.14-4.95 (m, 6H), 4.48 (s, 2H), 4.02-3.92 (m, 4H), 2.44-1.76 (m, 20H), 1.71-1.52 (m, 18H), 1.34-1.25 (m, 6H). CDCl$_3$ solvent peak: δ 7.24.

Example 23

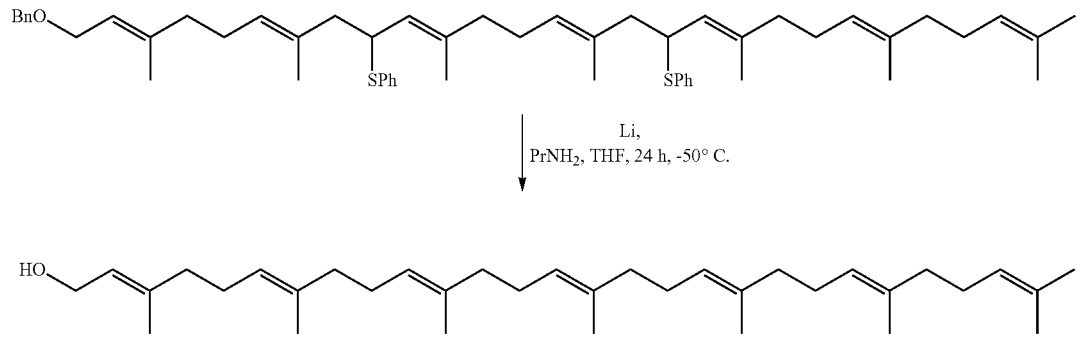

At −50° C., 0.16 g of Li-wire was added to 10 ml of propylamine and 1.57 g (1.96 mmol) dissolved in 16 ml of propylamine was added portion wise. The mixture was stirred at −50° C. for 24 h. Excess Li was removed and the blue color was dissipated by addition of 3-hexyne. To the resulting yellowish suspension, MeOH was added at −50° C. until a colourless suspension was obtained. The resulting salts were dissolved in water. The volatiles were removed by rotary evaporation and the residue was extracted with diethyl ether (3×30 ml). The combined organic extracts were dried over Na$_2$SO$_4$, filtered and concentrated in vacuo by rotary evaporation at 30° C. The crude product was further purified by flash column chromatography on SiO$_2$ using a mixture of heptane:EtOAc (9/1 v/v) as eluent.

Example 24

0.25 g (1.37 mmol) allyl sulfone was dissolved in 15 ml of dry THF and the solution was cooled to −78° C. with CO$_2$/MeOH. At −78° C., 0.80 ml (1.28 mmol) BuLi (1.6 M solution in hexane) was added drop wise via septum and syringe. The orange solution was stirred for 1 h at −78° C. 0.60 g (1.07 mmol) allylic bromide dissolved in 3 ml of dry THF was added via septum and syringe. The orange reaction mixture was allowed to reach room temperature within 1 h and at that temperature 0.10 g (0.89 mmol) KOtBu and 3 ml of dry tBuOH were added. The reaction mixture stirred at 0° C. for 1 h and 16 h at room temperature over night. The reaction was quenched by addition of 25 ml of brine and diluted with 25 ml of CH$_2$Cl$_2$. The layers were separated and the aqueous layer was extracted with CH$_2$Cl$_2$ (3×25 ml). The combined organic extracts were washed with brine, dried over Na$_2$SO$_4$, filtered and concentrated in vacuo by rotary evaporation at 30° C. The crude product was further purified by flash column chromatography on SiO$_2$ using heptane/EtOAc (95:5) as eluent to give yellow oil (0.50 g, 0.75 mmol, 71%).

$^1$H NMR (300 MHz, CDCl$_3$) δ 7.83-7.80 (m, 2H), 7.57-7.44 (m, 3H), 7.02 (q, $^3$J=7.1 Hz, 1H), 5.10-5.07 (m, 5H), 4.99-4.96 (m, 1H), 4.65-4.62 (m, 1H), 3.00 (d, $^3$J=6.5 Hz, 2H), 2.10-1.95 (m, 24H), 1.82 (d, $^3$J=7.1 Hz, 3H), 1.66 (s, 3H), 1.58 (s, 18H), 1.56 (s, 3H) CDCl$_3$ solvent peak: δ 7.24.

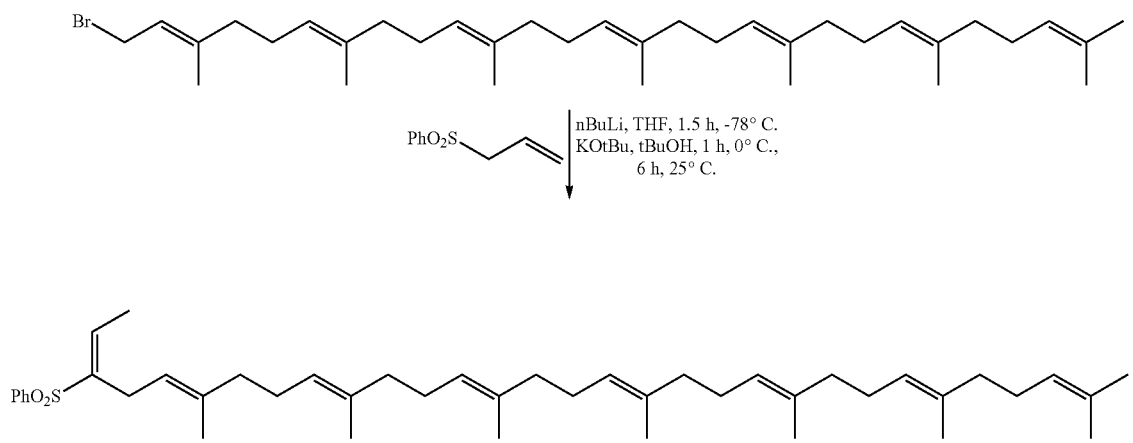

Example 25

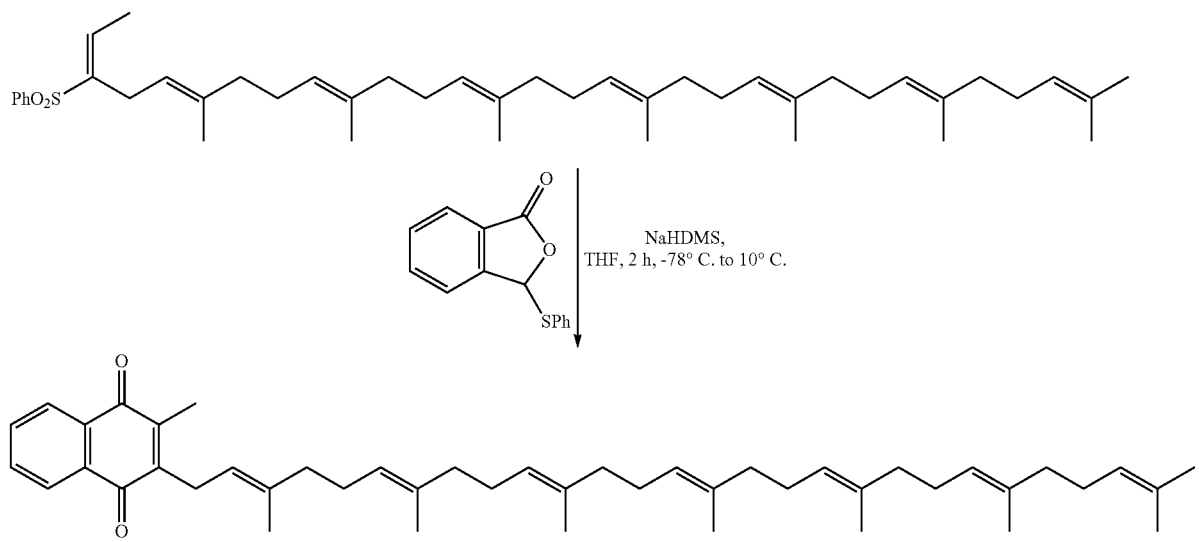

0.12 g (0.46 mmol) benzolactone was dissolved in 10 ml of dry THF and the solution was cooled to −78° C. with $CO_2$/MeOH. At −78° C., 1.00 ml (1.00 mmol) NaHDMS (1.0 M solution in THF) was added drop wise via septum and syringe and the resulting yellow solution was stirred for 0.5 h at −78° C. 0.42 g (0.64 mmol) sulfone dissolved in 3 ml of dry THF was added via septum and syringe in one portion. The orange reaction mixture was allowed to warm up to 10° C. over 1.5 h and then was cooled to 0° C. and quenched with 20 ml of $NH_4Cl$ solution and diluted with 25 ml of diethyl ether. The layers were separated and the aqueous layer was extracted with diethyl ether (3×25 ml). The combined organic extracts were washed with brine, dried over $Na_2SO_4$, filtered and concentrated in vacuo by rotary evaporation at 30° C. The crude product was further purified by flash column chromatography on $SiO_2$ using heptane/EtOAc (95:5) as eluent to give yellow oil (0.14 g, 0.22 mmol, 48%).

$^1$H NMR (200 MHz, $CDCl_3$) δ 8.07-8.00 (m, 2H), 7.69-7.63 (m, 2H), 5.08-4.97 (m, 7H), 3.35 (d, $^3J$=6.9 Hz, 2H) 2.16 (s, 3H), 2.05-1.81 (m, 24H), 1.77 (s, 3H), 1.65 (s, 3H), 1.57 (s, 12H), 1.54 (s, 6H); $^{13}$C NMR (50 MHz, $CDCl_3$) δ 185.34, 184.40, 146.08, 143.27, 137.48, 135.15, 134.84, 133.25, 133.19, 132.13, 132.09, 131.15, 126.24, 126.13, 124.37, 124.23, 124.11, 123.80, 119.05, 39.68, 26.72, 26.65, 26.45, 25.96, 25.65, 17.63, 16.38, 15.97, 12.62 $CDCl_3$ solvent peak: δ 7.24, 77.63, 77.00, 76.36.

The invention claimed is:
1. A process for the preparation of MK-7 comprising converting a compound

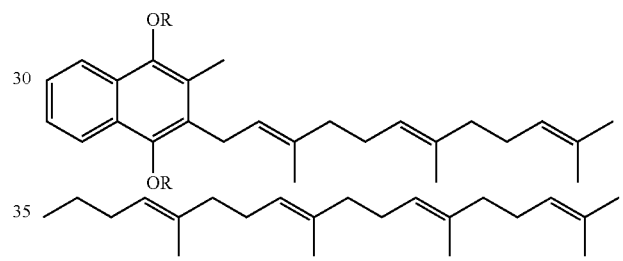

wherein R is an alkyl group;
into MK-7:

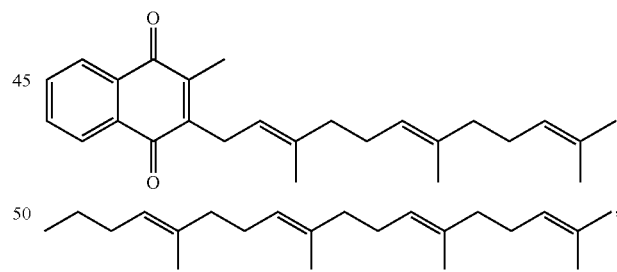

wherein conversion is achieved using cerium ammonium nitrate.

* * * * *